(12) United States Patent
Mukaddam et al.

(10) Patent No.: US 8,550,298 B2
(45) Date of Patent: Oct. 8, 2013

(54) MICROFLUIDIC DISPENSING ASSEMBLY

(75) Inventors: Kabir James Mukaddam, Cambridge, MA (US); Jeremy Stevenson, Lexington, MA (US)

(73) Assignee: Formulatrix, Inc., Waltham, MA (US)

( * ) Notice: Subject to any disclaimer, the term of this patent is extended or adjusted under 35 U.S.C. 154(b) by 528 days.

(21) Appl. No.: 12/369,950

(22) Filed: Feb. 12, 2009

(65) Prior Publication Data
US 2010/0186841 A1    Jul. 29, 2010

Related U.S. Application Data

(63) Continuation of application No. 12/358,607, filed on Jan. 23, 2009.

(51) Int. Cl.
| | |
|---|---|
| B67D 7/70 | (2010.01) |
| B67D 1/00 | (2006.01) |
| F16K 3/00 | (2006.01) |
| F15C 1/04 | (2006.01) |
| F17D 1/00 | (2006.01) |
| F17D 1/16 | (2006.01) |
| B01L 3/00 | (2006.01) |
| B01L 3/02 | (2006.01) |
| G01F 11/00 | (2006.01) |
| G01N 21/75 | (2006.01) |
| F15C 1/00 | (2006.01) |

(52) U.S. Cl.
USPC ............. 222/61; 222/1; 222/56; 222/255; 422/400; 422/501; 422/504; 422/505; 422/506; 422/521; 422/522; 422/537; 137/7; 137/14; 137/803; 137/831; 137/863

(58) Field of Classification Search
USPC .............. 422/400, 504–6, 516, 521–22, 537
See application file for complete search history.

(56) References Cited

U.S. PATENT DOCUMENTS

| | | | | |
|---|---|---|---|---|
| 4,649,967 | A | * | 3/1987 | Gruenstein et al. ............. 141/59 |
| 5,800,690 | A | | 9/1998 | Chow et al. |
| 5,842,787 | A | | 12/1998 | Kopf-Sill et al. |

(Continued)

FOREIGN PATENT DOCUMENTS

| | | |
|---|---|---|
| AU | 199868841 B2 | 10/1998 |
| AU | 200028936 B2 | 6/2000 |

(Continued)

OTHER PUBLICATIONS

European Search Report from European Application No. 08008428, dated Sep. 19, 2008.

(Continued)

*Primary Examiner* — Brian J Sines
*Assistant Examiner* — Jennifer Wecker
(74) *Attorney, Agent, or Firm* — Wolf, Greenfield & Sacks, P.C.

(57) ABSTRACT

A microfluidic dispensing system may include multiple supply lines for simultaneous filling of diaphragm pumps associated with each supply line. Each supply line may fill corresponding groups of diaphragm pumps with a corresponding ingredient to a supply reservoir for the supply line. Accordingly, different groups of diaphragm pumps corresponding to different supply lines may be filled with corresponding ingredients simultaneously. Those ingredients corresponding to the different groups of diaphragm pumps may also be dispensed simultaneously, giving rise to a faster and more efficient fluidic dispensing system.

14 Claims, 21 Drawing Sheets

(56) References Cited

U.S. PATENT DOCUMENTS

| | | | |
|---|---|---|---|
| 5,869,004 A | 2/1999 | Parce et al. |
| 5,876,675 A | 3/1999 | Kennedy |
| 5,959,291 A | 9/1999 | Jensen |
| 5,964,995 A | 10/1999 | Nikiforov et al. |
| 5,976,336 A | 11/1999 | Dubrow et al. |
| 5,989,402 A | 11/1999 | Chow et al. |
| 6,012,902 A | 1/2000 | Parce |
| 6,074,725 A | 6/2000 | Kennedy |
| 6,086,740 A | 7/2000 | Kennedy |
| 6,117,396 A | 9/2000 | Demers |
| 6,148,508 A | 11/2000 | Wolk |
| 6,149,787 A | 11/2000 | Chow et al. |
| 6,150,119 A | 11/2000 | Kopf-Sill et al. |
| 6,227,824 B1 | 5/2001 | Stehr |
| 6,235,471 B1 | 5/2001 | Knapp et al. |
| 6,274,089 B1 | 8/2001 | Chow et al. |
| 6,283,730 B1 | 9/2001 | Sasaki et al. |
| 6,322,683 B1 | 11/2001 | Wolk et al. |
| 6,357,141 B1 | 3/2002 | Kearsley et al. |
| 6,391,622 B1 | 5/2002 | Knapp et al. |
| 6,403,338 B1 | 6/2002 | Knapp et al. |
| 6,406,893 B1 | 6/2002 | Knapp et al. |
| 6,440,722 B1 | 8/2002 | Knapp et al. |
| 6,444,461 B1 | 9/2002 | Knapp et al. |
| 6,458,259 B1 | 10/2002 | Parce et al. |
| 6,468,763 B1 | 10/2002 | Farinas |
| 6,481,453 B1 | 11/2002 | O'Connor et al. |
| 6,500,323 B1 | 12/2002 | Chow et al. |
| 6,506,609 B1 | 1/2003 | Wada et al. |
| 6,521,188 B1 | 2/2003 | Webster |
| 6,529,835 B1 | 3/2003 | Wada et al. |
| 6,613,580 B1 | 9/2003 | Chow et al. |
| 6,615,856 B2 | 9/2003 | McNeely et al. |
| 6,619,311 B2 | 9/2003 | O'Connor et al. |
| 6,635,487 B1 | 10/2003 | Lee et al. |
| 6,674,525 B2 | 1/2004 | Bardell et al. |
| D486,156 S | 2/2004 | Lee et al. |
| D488,818 S | 4/2004 | Lee et al. |
| 6,720,148 B1 | 4/2004 | Nikiforov |
| 6,733,645 B1 | 5/2004 | Chow |
| 6,748,978 B2 | 6/2004 | Pezzuto et al. |
| 6,801,875 B1 | 10/2004 | Wolk et al. |
| 6,827,095 B2 | 12/2004 | O'Connor et al. |
| 6,827,113 B2 | 12/2004 | Downs et al. |
| 6,849,411 B2 | 2/2005 | Knapp et al. |
| 6,858,185 B1 | 2/2005 | Kopf-Sill et al. |
| 6,951,632 B2 | 10/2005 | Unger et al. |
| 6,977,163 B1 | 12/2005 | Mehta |
| 7,001,853 B1 | 2/2006 | Brown et al. |
| 7,024,281 B1 | 4/2006 | Unno |
| 7,036,917 B2 | 5/2006 | Muller-Chorus et al. |
| 7,038,472 B1 | 5/2006 | Chien |
| 7,052,594 B2 | 5/2006 | Pelrine et al. |
| 7,060,171 B1 | 6/2006 | Nikiforov et al. |
| 7,069,952 B1 | 7/2006 | McReynolds et al. |
| 7,077,152 B2 | 7/2006 | Karp |
| 7,150,999 B1 | 12/2006 | Shuck |
| 7,153,421 B2 | 12/2006 | Koehler et al. |
| 7,161,356 B1 | 1/2007 | Chien |
| 7,178,386 B1 | 2/2007 | Gamble et al. |
| 7,208,125 B1 | 4/2007 | Dong |
| 7,284,966 B2 | 10/2007 | Xu et al. |
| 7,445,926 B2 * | 11/2008 | Mathies et al. ............ 435/288.5 |
| 2001/0017158 A1 * | 8/2001 | Kamholz et al. ............ 137/251.1 |
| 2001/0020589 A1 | 9/2001 | Kopf-Sill |
| 2001/0026929 A1 | 10/2001 | Yang et al. |
| 2001/0027918 A1 | 10/2001 | Parce et al. |
| 2001/0033796 A1 | 10/2001 | Unger et al. |
| 2001/0036626 A1 | 11/2001 | Farinas et al. |
| 2001/0045358 A1 | 11/2001 | Kopf-Sill et al. |
| 2001/0049148 A1 | 12/2001 | Wolk et al. |
| 2001/0051338 A1 | 12/2001 | Chan et al. |
| 2001/0052460 A1 | 12/2001 | Chien et al. |
| 2002/0001856 A1 | 1/2002 | Chow et al. |
| 2002/0003177 A1 | 1/2002 | O'Connor et al. |
| 2002/0004182 A1 | 1/2002 | McReynolds |
| 2002/0009392 A1 | 1/2002 | Wolk et al. |
| 2002/0009711 A1 | 1/2002 | Wada et al. |
| 2002/0012971 A1 | 1/2002 | Mehta |
| 2002/0017464 A1 | 2/2002 | Parce et al. |
| 2002/0019059 A1 | 2/2002 | Chow et al. |
| 2002/0023684 A1 | 2/2002 | Chow |
| 2002/0025280 A1 | 2/2002 | Chazan et al. |
| 2002/0033337 A1 | 3/2002 | Ausserer et al. |
| 2002/0034580 A1 | 3/2002 | Yang et al. |
| 2002/0037520 A1 | 3/2002 | Nikiforov et al. |
| 2002/0039280 A1 | 4/2002 | O'Connor et al. |
| 2002/0041375 A1 | 4/2002 | Jensen et al. |
| 2002/0046948 A1 | 4/2002 | Chow et al. |
| 2002/0048768 A1 | 4/2002 | Nikiforov |
| 2002/0049694 A1 | 4/2002 | Parce |
| 2002/0052696 A1 | 5/2002 | Gallagher et al. |
| 2002/0055149 A1 | 5/2002 | Kopf-Sill |
| 2002/0064880 A1 * | 5/2002 | Merten et al. .................. 436/43 |
| 2002/0076697 A1 | 6/2002 | Nikiforov |
| 2002/0079008 A1 | 6/2002 | Chien et al. |
| 2002/0081222 A1 | 6/2002 | Karp |
| 2002/0084185 A1 | 7/2002 | Sundberg et al. |
| 2002/0086340 A1 | 7/2002 | Veerapandian et al. |
| 2002/0086439 A1 | 7/2002 | Nagle et al. |
| 2002/0092973 A1 | 7/2002 | Nagle et al. |
| 2002/0097398 A1 | 7/2002 | Parce |
| 2002/0108096 A1 | 8/2002 | Lee et al. |
| 2002/0110926 A1 | 8/2002 | Kopf-Sill et al. |
| 2002/0112961 A1 | 8/2002 | O'Connor et al. |
| 2002/0117517 A1 | 8/2002 | Unger et al. |
| 2002/0119536 A1 | 8/2002 | Stern |
| 2002/0123133 A1 | 9/2002 | Mehta et al. |
| 2002/0124896 A1 | 9/2002 | O'Connor et al. |
| 2002/0125139 A1 | 9/2002 | Chow et al. |
| 2002/0127149 A1 | 9/2002 | Dubrow et al. |
| 2002/0128593 A1 | 9/2002 | Sjolander et al. |
| 2002/0132265 A1 | 9/2002 | Kopf-Sill |
| 2002/0138209 A1 | 9/2002 | Gallagher |
| 2002/0142618 A1 | 10/2002 | Parce et al. |
| 2002/0144774 A1 | 10/2002 | McReynolds |
| 2002/0144895 A1 | 10/2002 | Stern et al. |
| 2002/0153046 A1 | 10/2002 | Dantsker et al. |
| 2002/0153047 A1 | 10/2002 | Parce et al. |
| 2002/0155010 A1 | 10/2002 | Karp et al. |
| 2002/0158022 A1 | 10/2002 | Huang et al. |
| 2002/0159919 A1 | 10/2002 | Churchill et al. |
| 2002/0160139 A1 | 10/2002 | Huang et al. |
| 2002/0166582 A1 | 11/2002 | O'Connor et al. |
| 2002/0166585 A1 | 11/2002 | O'Connor et al. |
| 2002/0166768 A1 | 11/2002 | Dubrow |
| 2002/0177238 A1 | 11/2002 | Karp et al. |
| 2002/0179445 A1 | 12/2002 | Alajoki et al. |
| 2002/0180963 A1 | 12/2002 | Chien et al. |
| 2002/0187074 A1 | 12/2002 | O'Connor et al. |
| 2002/0187513 A1 | 12/2002 | Kopf-Sill et al. |
| 2002/0187560 A1 | 12/2002 | Pezzuto et al. |
| 2002/0187564 A1 | 12/2002 | Chow et al. |
| 2002/0192719 A1 | 12/2002 | Nikiforov et al. |
| 2002/0197603 A1 | 12/2002 | Chow et al. |
| 2002/0197630 A1 | 12/2002 | Knapp et al. |
| 2002/0198694 A1 | 12/2002 | Yang et al. |
| 2003/0003026 A1 | 1/2003 | Parce et al. |
| 2003/0005967 A1 | 1/2003 | Karp et al. |
| 2003/0011382 A1 | 1/2003 | Chow et al. |
| 2003/0015429 A1 | 1/2003 | Dubrow et al. |
| 2003/0015672 A1 | 1/2003 | Gallagher |
| 2003/0017085 A1 | 1/2003 | Kercso et al. |
| 2003/0021725 A1 | 1/2003 | Unno et al. |
| 2003/0027225 A1 | 2/2003 | Wada et al. |
| 2003/0027345 A1 | 2/2003 | Friswell et al. |
| 2003/0036080 A1 | 2/2003 | Jensen et al. |
| 2003/0080442 A1 | 5/2003 | Unger |
| 2003/0094953 A1 | 5/2003 | Brooks et al. |
| 2003/0104466 A1 | 6/2003 | Knapp et al. |
| 2003/0116738 A1 | 6/2003 | O'Connor et al. |
| 2003/0124736 A1 | 7/2003 | Manz et al. |
| 2003/0129756 A1 | 7/2003 | Thorne, IV et al. |
| 2003/0138359 A1 | 7/2003 | Chow et al. |

| | | |
|---|---|---|
| 2003/0138829 A1 | 7/2003 | Unger et al. |
| 2003/0148922 A1 | 8/2003 | Knapp et al. |
| 2003/0150555 A1 | 8/2003 | Gandhi et al. |
| 2003/0159742 A1 | 8/2003 | Karp et al. |
| 2003/0170903 A1 | 9/2003 | Johnson et al. |
| 2003/0186295 A1 | 10/2003 | Colin et al. |
| 2003/0198576 A1 | 10/2003 | Coyne et al. |
| 2003/0215855 A1 | 11/2003 | Dubrow et al. |
| 2003/0215862 A1 | 11/2003 | Parce et al. |
| 2003/0215957 A1 | 11/2003 | Lemmo et al. |
| 2003/0230486 A1 | 12/2003 | Chien et al. |
| 2004/0005247 A1 | 1/2004 | Karp |
| 2004/0009545 A1 | 1/2004 | Farinas et al. |
| 2004/0018115 A1 | 1/2004 | Karp |
| 2004/0019300 A1 | 1/2004 | Leonard |
| 2004/0026617 A1 | 2/2004 | Gregori et al. |
| 2004/0028559 A1 | 2/2004 | Schuck |
| 2004/0048299 A1 | 3/2004 | Parce et al. |
| 2004/0048360 A1 | 3/2004 | Wada et al. |
| 2004/0053315 A1 | 3/2004 | Spaid et al. |
| 2004/0053422 A1 | 3/2004 | Chan et al. |
| 2004/0067597 A1 | 4/2004 | Datwani et al. |
| 2004/0072278 A1 | 4/2004 | Chou et al. |
| 2004/0080744 A1 | 4/2004 | Hobbs |
| 2004/0089057 A1 | 5/2004 | Hobbs et al. |
| 2004/0092033 A1 | 5/2004 | Gustafson et al. |
| 2004/0118189 A1 | 6/2004 | Karp et al. |
| 2004/0179972 A1 | 9/2004 | Karp et al. |
| 2004/0180377 A1 | 9/2004 | Manger et al. |
| 2004/0203055 A1 | 10/2004 | Kennedy et al. |
| 2004/0208794 A1 | 10/2004 | Karg et al. |
| 2004/0209381 A1 | 10/2004 | Peters et al. |
| 2004/0217279 A1 | 11/2004 | Hobbs et al. |
| 2004/0224325 A1 | 11/2004 | Knapp et al. |
| 2004/0226884 A1 | 11/2004 | O'Connor et al. |
| 2004/0238401 A1 | 12/2004 | Greenstein et al. |
| 2004/0253545 A1 | 12/2004 | David |
| 2005/0003554 A1 | 1/2005 | Brasseur |
| 2005/0006238 A1 | 1/2005 | Jaffe |
| 2005/0011764 A1 | 1/2005 | Berndt et al. |
| 2005/0019792 A1 | 1/2005 | McBride et al. |
| 2005/0019794 A1 | 1/2005 | Nassef et al. |
| 2005/0032238 A1 | 2/2005 | Karp et al. |
| 2005/0056713 A1 | 3/2005 | Tisone et al. |
| 2005/0064465 A1 | 3/2005 | Dettloff et al. |
| 2005/0118073 A1 | 6/2005 | Facer et al. |
| 2005/0121324 A1 | 6/2005 | Park et al. |
| 2005/0133370 A1 | 6/2005 | Park et al. |
| 2005/0148093 A1 | 7/2005 | Chien |
| 2005/0170362 A1 | 8/2005 | Wada et al. |
| 2005/0182573 A1 | 8/2005 | Tripathi et al. |
| 2005/0197652 A1 | 9/2005 | Nat |
| 2005/0202470 A1 | 9/2005 | Sundberg et al. |
| 2005/0221385 A1 | 10/2005 | Nikiforov et al. |
| 2005/0250199 A1* | 11/2005 | Anderson et al. .......... 435/287.2 |
| 2005/0257885 A1 | 11/2005 | Hobbs |
| 2005/0282175 A1 | 12/2005 | Taylor et al. |
| 2006/0006067 A1 | 1/2006 | Unger |
| 2006/0024751 A1 | 2/2006 | May et al. |
| 2006/0062696 A1 | 3/2006 | Chow et al. |
| 2006/0073035 A1 | 4/2006 | Sundararajan |
| 2006/0076068 A1 | 4/2006 | Young et al. |
| 2006/0211055 A1 | 9/2006 | Hafeman et al. |
| 2006/0227325 A1 | 10/2006 | Rulison et al. |
| 2006/0239860 A1 | 10/2006 | Evers et al. |
| 2006/0246493 A1 | 11/2006 | Jensen et al. |
| 2006/0246533 A1 | 11/2006 | Fathollahi et al. |
| 2007/0003447 A1 | 1/2007 | Gleason et al. |
| 2007/0048188 A1* | 3/2007 | Bigus .......................... 422/100 |
| 2007/0052781 A1 | 3/2007 | Fraden et al. |
| 2007/0053799 A1 | 3/2007 | Bousse et al. |
| 2007/0059208 A1 | 3/2007 | Desmond |
| 2007/0059319 A1 | 3/2007 | Carlson et al. |
| 2007/0074972 A1 | 4/2007 | Nassef et al. |
| 2007/0080063 A1 | 4/2007 | Kennedy et al. |
| 2007/0086922 A1 | 4/2007 | Andersson et al. |
| 2007/0092975 A1 | 4/2007 | Potyrailo et al. |
| 2007/0099200 A1 | 5/2007 | Chow et al. |
| 2007/0166199 A1* | 7/2007 | Zhou et al. ................... 422/100 |
| 2007/0183935 A1 | 8/2007 | Clemmens et al. |
| 2008/0134804 A1* | 6/2008 | Maeda et al. .............. 73/863.01 |
| 2009/0010810 A1* | 1/2009 | Krug et al. ................... 422/100 |
| 2009/0020556 A1* | 1/2009 | Mukaddam et al. .......... 222/56 |
| 2009/0061428 A1 | 3/2009 | McBride et al. |

FOREIGN PATENT DOCUMENTS

| | | |
|---|---|---|
| AU | 200071755 B2 | 3/2001 |
| AU | 200124770 B2 | 5/2001 |
| AU | 200118420 B2 | 8/2001 |
| AU | 2007200710 A1 | 3/2007 |
| CA | 2284612 A1 | 10/1998 |
| EP | 0 465 229 A | 1/1992 |
| EP | 0 703 364 A | 3/1996 |
| JP | 2000-220766 A | 8/2000 |
| JP | 2003-75407 A | 3/2003 |
| JP | 2004-230469 A | 8/2004 |
| JP | 2005-49357 A | 2/2005 |
| JP | 2005-509113 T | 4/2005 |
| JP | 2007-102573 A | 4/2007 |
| WO | WO 98/38622 A1 | 9/1998 |
| WO | WO 98/45481 A1 | 10/1998 |
| WO | WO 99/64840 A1 | 12/1999 |
| WO | WO 00/43748 A | 7/2000 |
| WO | WO 00/70353 A2 | 11/2000 |
| WO | WO 02/04926 A2 | 2/2002 |
| WO | WO 02/30486 A2 | 4/2002 |
| WO | WO 02/055198 A | 7/2002 |
| WO | WO 02/060582 A2 | 8/2002 |
| WO | WO 2004/009238 A1 | 1/2004 |
| WO | WO 2004/103563 A2 | 12/2004 |
| WO | WO 2005/072858 A1 | 8/2005 |
| WO | WO 2005/114223 A2 | 12/2005 |
| WO | WO 2006/060748 A2 | 6/2006 |
| WO | WO 2006/062805 A2 | 6/2006 |
| WO | WO 2006/121786 A1 | 11/2006 |
| WO | WO 2006/127191 A2 | 11/2006 |
| WO | WO 2007/033385 A2 | 3/2007 |
| WO | WO 2007/041619 A2 | 4/2007 |
| WO | WO 2007/044091 A2 | 4/2007 |
| WO | WO 2007/044432 A2 | 4/2007 |
| WO | WO 2007/044938 A2 | 4/2007 |
| WO | WO 2007/064404 A2 | 6/2007 |
| WO | WO 2007/064635 A1 | 6/2007 |
| WO | WO 2008/089493 A2 | 7/2008 |

OTHER PUBLICATIONS

European Search Report from European Application No. 08008429, dated Sep. 22, 2008.

European Search Report from European Application No. 08008435, dated Sep. 23, 2008.

European Search Report from European Application No. 10150624, dated Mar. 18, 2010.

* cited by examiner

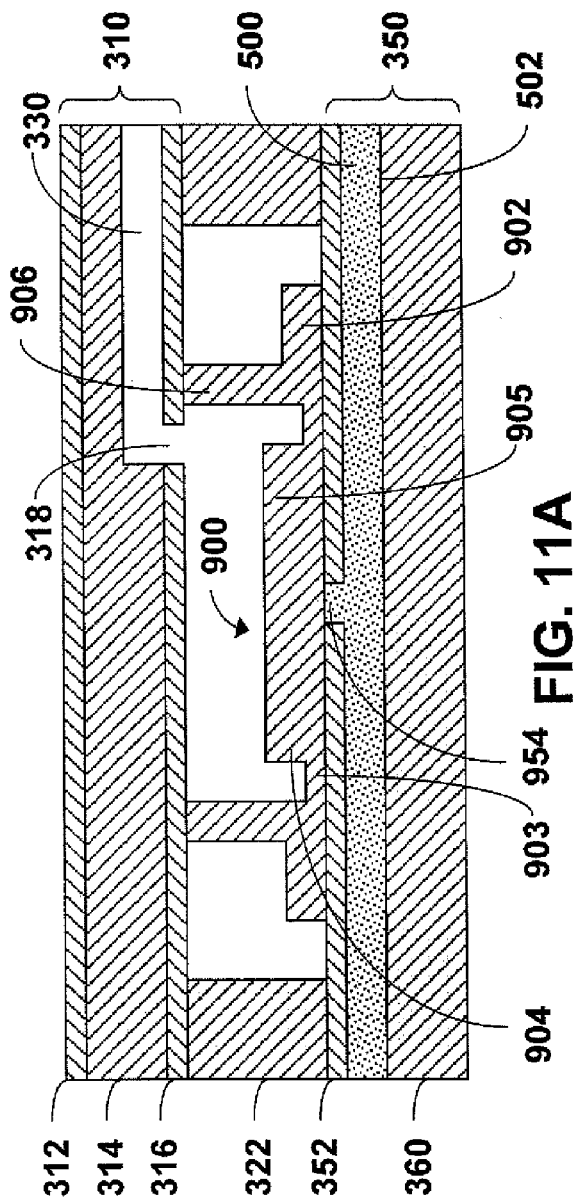
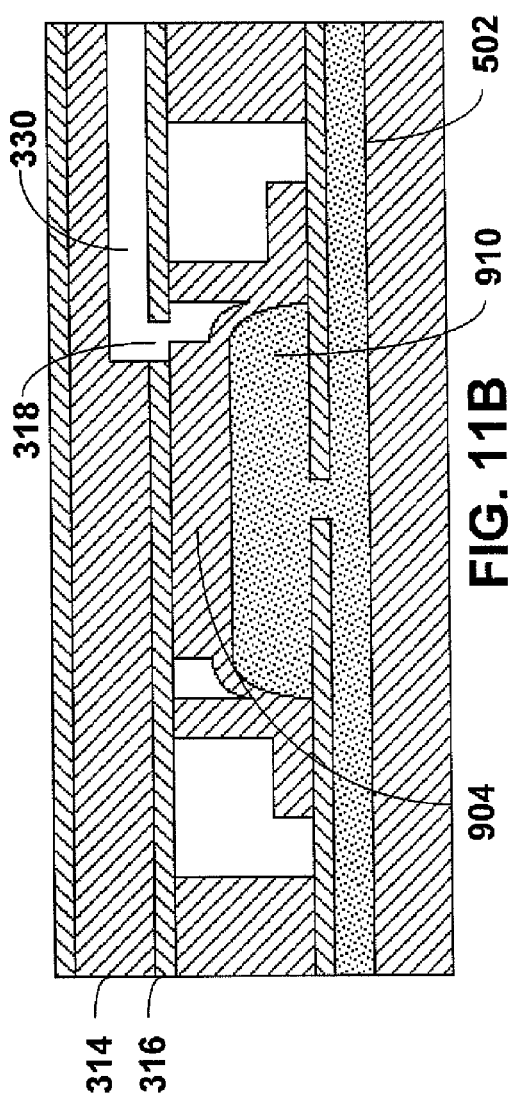

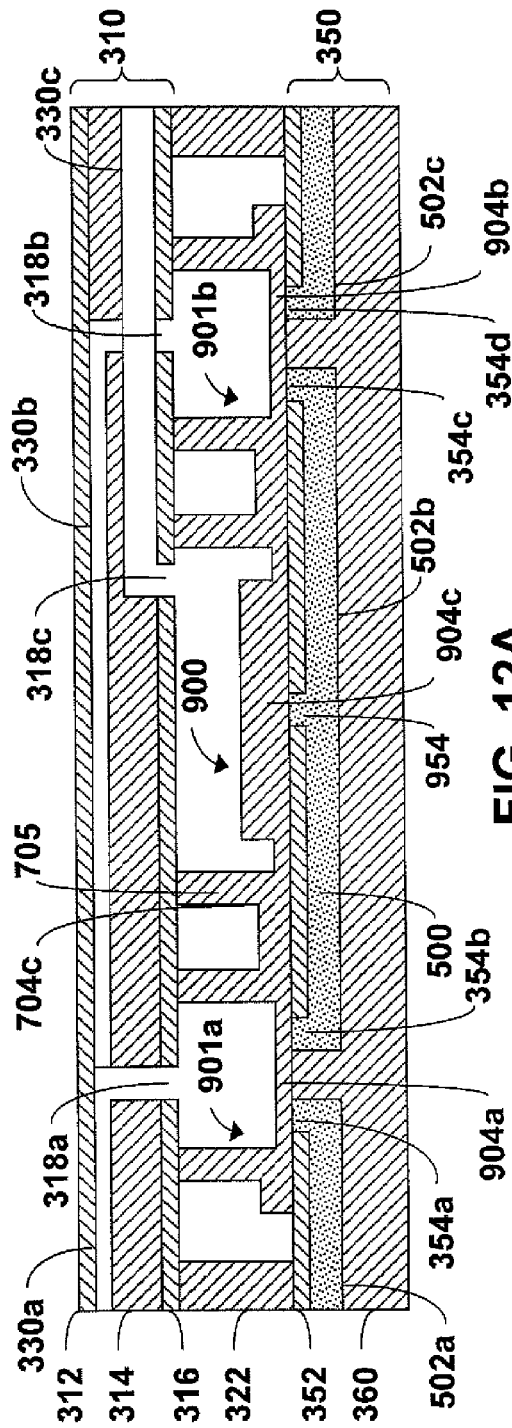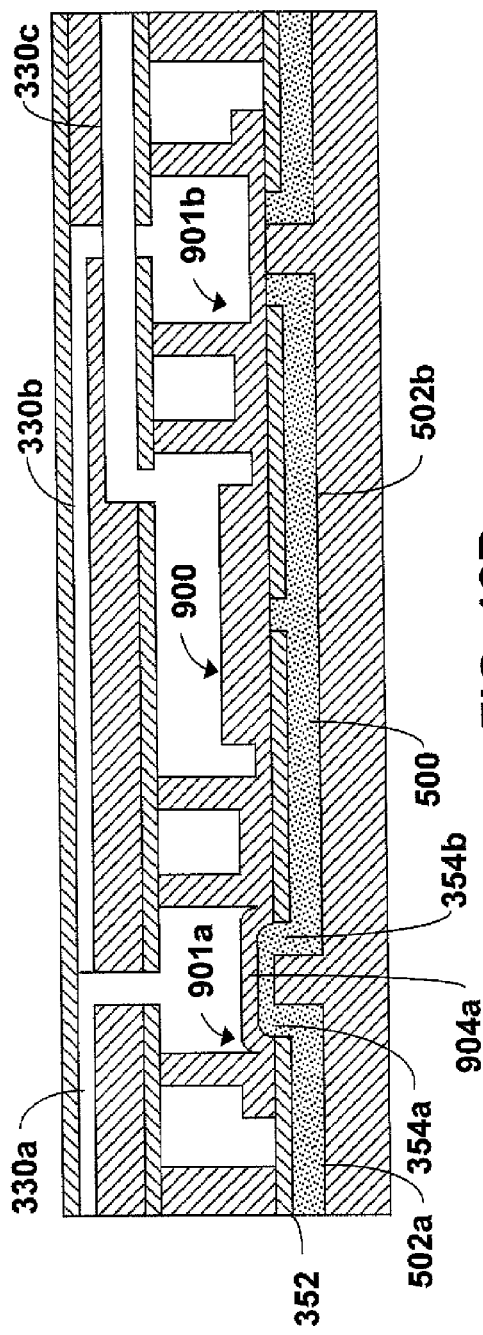
FIG. 12A
FIG. 12B

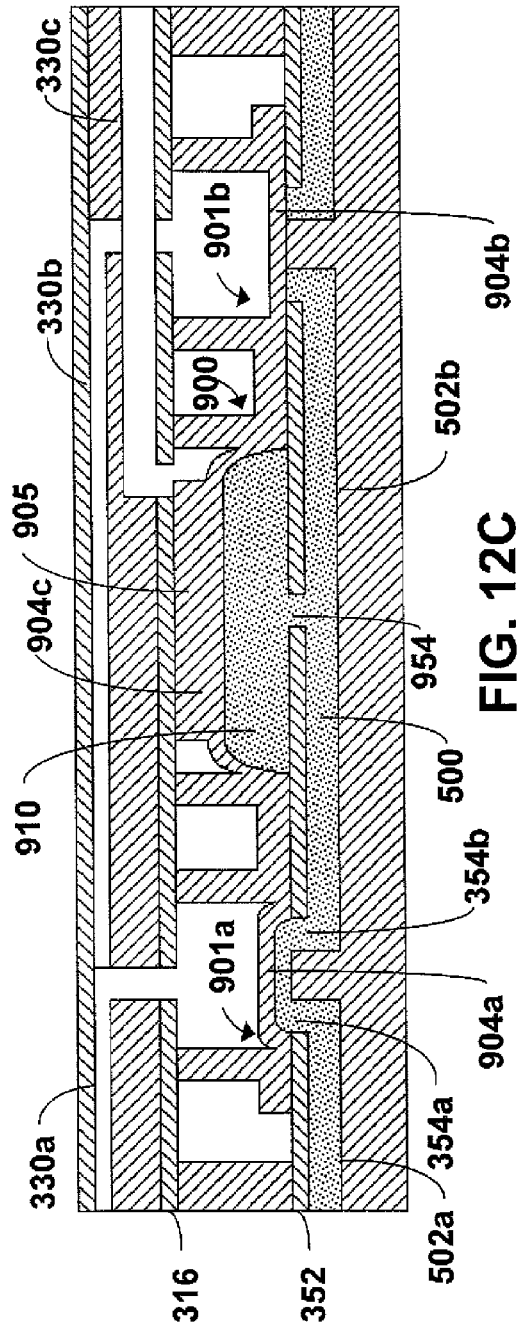
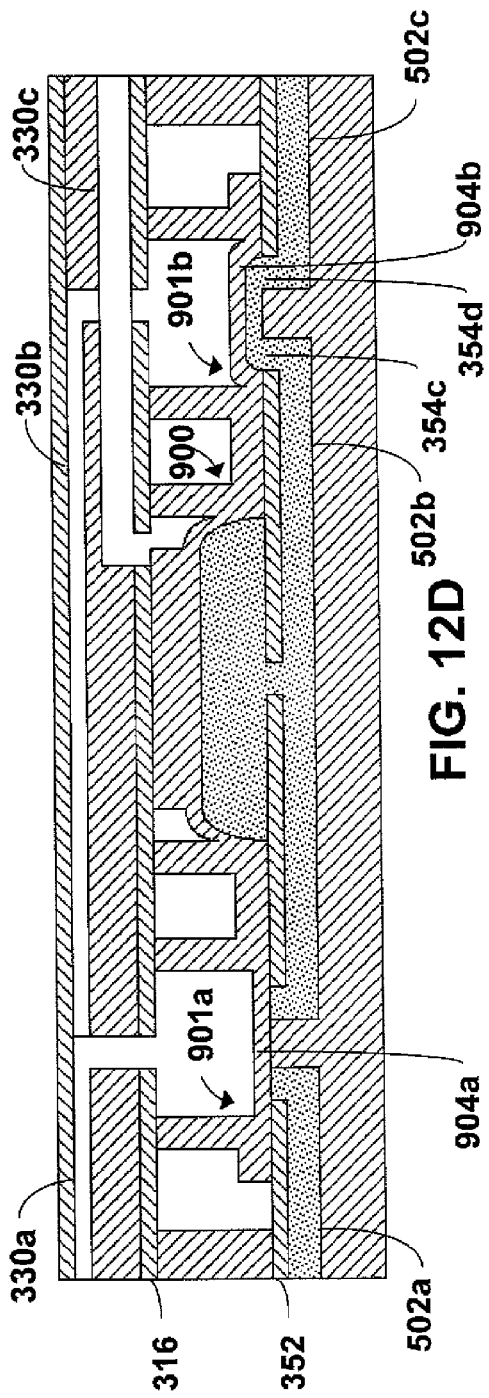
FIG. 12C
FIG. 12D

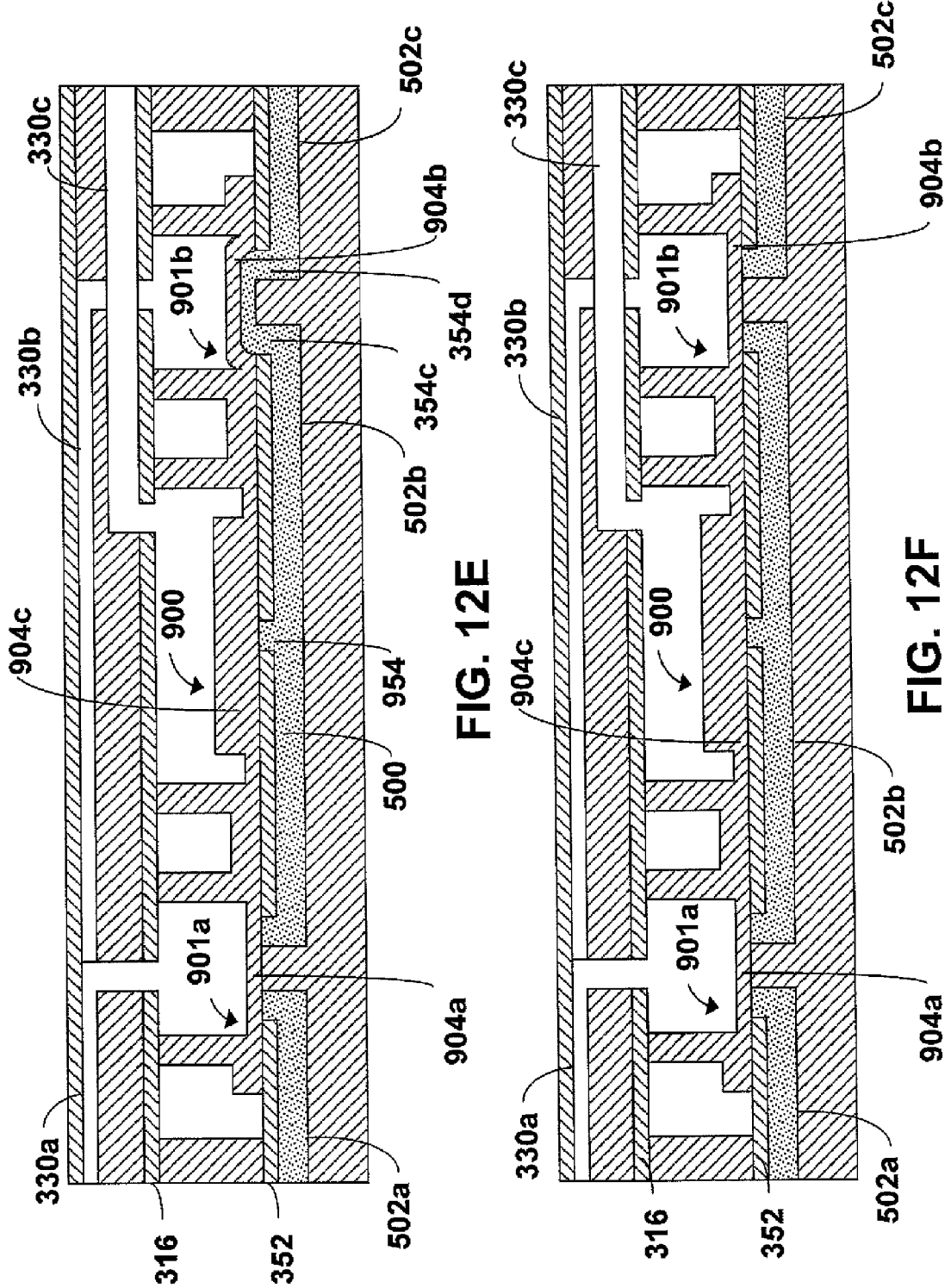

MICROFLUIDIC DISPENSING ASSEMBLY

CROSS-REFERENCE TO RELATED APPLICATIONS

This application is a continuation of and claims the benefit under 35 U.S.C. §120 of co-pending U.S. application Ser. No. 12/358,607 titled "MICROFLUIDIC DISPENSING ASSEMBLY" filed Jan. 23, 2009, which is herein incorporated by reference in its entirety.

BACKGROUND

1. Field

Apparatuses and methods for making the process of dispensing selected fluid ingredients in any combination of specified discrete volumes quickly and efficiently is disclosed.

2. Discussion of Related Art

Challenges exist in designing fluid handling devices where often competing criteria must be met. In this regard, producing a fluid handling device that can effectively deliver fluid quickly and efficiently while being small and compact is challenging. For example, when dispensing fluid to a microplate, such as those used in chemical and/or biological analyses, the fluid must be dispensed at a relatively high throughput and in a compact arrangement. Various arrangements exist that attempt to meet these often competing criteria.

SUMMARY

In one illustrative embodiment, a microfluidic dispensing system is provided. The system comprises a plurality of diaphragm pumps, each of the plurality of diaphragm pumps being actuated upon application of a corresponding pressure control pump signal, and each of the plurality of diaphragm pumps being adapted to pump a fixed volume of fluid; a plurality of supply lines, each of the supply lines being in fluid communication with at least one of the diaphragm pumps for simultaneously supplying a corresponding ingredient to the at least one of the diaphragm pumps, wherein the corresponding ingredient comes from a supply reservoir corresponding to each of the supply lines; and an array of nozzles in fluid communication with the at least one of the diaphragm pumps for simultaneously dispensing the corresponding ingredient in each of the at least one of the diaphragm pumps upon application of the corresponding pressure control pump signal.

In another illustrative embodiment, a fluidic connector assembly is provided. The assembly comprises a supply inlet; a magnetic inlet coupler disposed adjacent to the supply inlet; a supply outlet for providing a fluid ingredient to the supply inlet when the supply outlet is in fluid communication with the supply inlet; and a magnetic outlet coupler disposed adjacent to the supply outlet, wherein upon magnetic coupling of the magnetic outlet coupler and the magnetic inlet coupler, a seal is formed, the seal bringing the supply outlet in fluid communication with the supply inlet.

In a further illustrative embodiment, a method of microfluidic dispensing of a plurality of ingredients is provided. The method comprises providing a plurality of supply reservoirs, each of the plurality of supply reservoirs storing an ingredient; providing a supply line corresponding to each of the plurality of supply reservoirs; supplying the ingredients of the supply reservoirs to a plurality of corresponding diaphragm pumps via the supply line, each supply line being in fluid communication with the corresponding diaphragm pumps; simultaneously filling each of the corresponding diaphragm pumps with a corresponding ingredient, the corresponding ingredient being supplied from the supply line corresponding to each of the plurality of supply reservoirs, wherein upon actuation of the corresponding diaphragm pump with a fill pressure control pump signal, the corresponding ingredient fills the corresponding diaphragm pump; and simultaneously dispensing the corresponding ingredient in each of the corresponding diaphragm pumps through a nozzle, wherein upon actuation of the corresponding diaphragm pump with a dispense pressure control pump signal, the corresponding ingredient exits the corresponding diaphragm pump.

Various embodiments of the present invention provide certain advantages. Not all embodiments of the invention share the same advantages and those that do may not share them under all circumstances.

Further features and advantages of the present invention, as well as the structure of various embodiments of the present invention are described in detail below with reference to the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 11A and 11B are schematic cross-sectional views of an alternative embodiment of an arrangement for moving fluid;

FIGS. 12A-12F are schematic cross-sectional views of another alternative embodiment of an arrangement for moving fluid;

DETAILED DESCRIPTION

Figure 1:
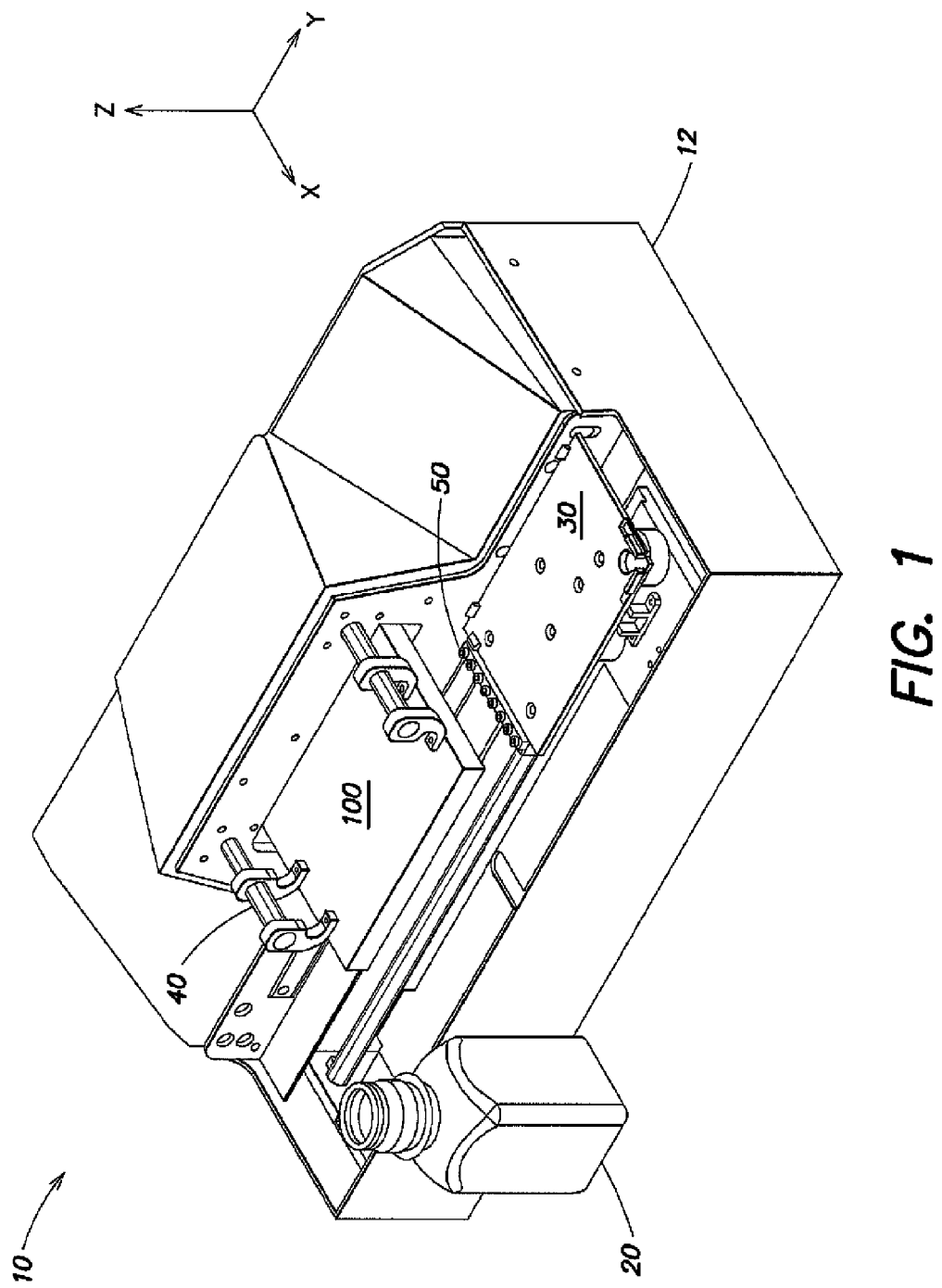
FIG. 1 is a perspective view of a microfluidic dispensing system according to one embodiment.

The inventions are not limited in its application to the details of construction and the arrangement of components set forth in the following description or illustrated in the drawings. Other embodiments may be employed and aspects of the inventions may be practiced or be carried out in various ways. Also, the phraseology and terminology used herein is for the purpose of description and should not be regarded as limiting. The use of "including," "comprising," "having," "containing," "involving," and/or variations thereof herein, is meant to encompass the items listed thereafter and equivalents thereof as well as additional items.

Aspects of the inventions are directed to a microfluidic dispensing system that includes arrangement(s) and/or technique(s) for making the process of dispensing selected fluid ingredients in any combination of specified discrete volumes quick and efficient.

In one aspect, the microfluidic dispensing system may include multiple supply lines for simultaneous filling of diaphragm pumps associated with each supply line. Each supply line may fill corresponding groups of diaphragm pumps with a corresponding ingredient to a supply reservoir for the supply line. Accordingly, different groups of diaphragm pumps corresponding to different supply lines may be filled with corresponding ingredients simultaneously. Those ingredients corresponding to the different groups of diaphragm pumps may also be dispensed simultaneously, giving rise to a faster and more efficient fluidic dispensing system.

In another aspect, the microfluidic dispensing system may include diaphragm pumps that may be used for aspirating in corresponding ingredients via a nozzle or a tip from supply sources. Tips may be placed in contact with ingredient supply sources, and through repeated actuation of the diaphragm pumps, desired volumes of ingredients are aspirated into the tips. In some cases, an air plug is aspirated into the tips before an ingredient. Once the desired volume of each ingredient is reached within each tip, the ingredients are dispensed from the tips through repeated actuation of corresponding diaphragm pumps.

The microfluidic dispensing system can include a number of pump regions and control components cooperating with the pump regions. The microfluidic dispensing system can also include a number of control elements associated with components corresponding to the pump regions. Aspects discussed herein are also related to commonly owned co-pending U.S. application Ser. No. 11/880,112, entitled "Metering Assembly and Method of Dispensing Fluid"; and commonly owned co-pending U.S. application Ser. No. 11/952,683, entitled "Metering Assembly and Method of Dispensing Fluid", both of which are hereby incorporated by reference herein in their entireties.

As described herein, it should be understood that when any number of components are said to be in "fluid communication", fluid may be permitted to pass between each of the components. In some cases, a valve may be located between components that are in fluid communication. In an open state, the valve may permit fluid to pass between each of the components. In a closed state, the valve may restrict fluid from passing between each of the components. However, whether or not the valve permits or restrict fluid flow between components, it should be appreciated that as used herein, the components are considered to be in "fluid communication".

The microfluidic dispensing system includes a microfluidic chip having diaphragm pumps within pump regions. In one embodiment, diaphragm pumps enable filling and dispensing of discrete volumes of ingredients through outlets such as, for example, nozzles and/or tips. Supply lines may be associated with diaphragm pumps in the pump regions, providing an arrangement for delivering corresponding ingredients to diaphragm pumps, with the ingredients coming from supply reservoirs. Along with diaphragm pumps, pump regions may include fluid channels that serve to provide a passageway for a fluid between various components associated with a pump region. For example, a fluid channel may provide fluid communication between a supply line, a diaphragm pump, and an outlet within a pump region. Pump regions may also include valves that may provide for opening and closing of fluid channels that lead to and from diaphragm pumps. Although valves may allow for control of ingredients flowing to and from diaphragm pumps, other arrangements for controlling fluid flow may be employed, as the inventions are not limited in this respect. Diaphragm pumps and valves may be controlled by any suitable method, such as, for example, a pressure control approach, as described further below, as the inventions are not limited in this respect.

In one embodiment, a number of diaphragm pumps may be supplied with corresponding ingredients for particular diaphragm pumps via supply lines that are in fluid communication with supply reservoirs for the corresponding ingredients. In the previously cited application, U.S. application Ser. No. 11/952,683, ingredients for supplying diaphragm pumps for eventual dispensing of those ingredients are supplied via one main supply line. In this regard, for the previous application, diaphragm pumps that are desired to be filled simultaneously may only be filled with one ingredient at a time. In order to input a different ingredient into the system for subsequent dispensing, the microfluidic dispensing system, including associated diaphragm pumps, valves, supply lines, and outlets would require a wash step in order to purge the system of residual ingredient. Once the system is rid of the former ingredient, a new ingredient may then be introduced. In the current application, in one embodiment, multiple supply lines allow for simultaneous filling of diaphragm pumps associated with each supply line with different ingredients, as desired. Accordingly, different ingredients that correspond to a particular group of diaphragm pumps may be dispensed simultaneously along with other ingredients that correspond to another group of diaphragm pumps. As a result, simultaneously filling different groups of diaphragm pumps with different ingredients corresponding to each group, and simultaneous dispense of those ingredients, may provide for a faster and more efficient fluidic dispensing system than previously considered.

In another embodiment, a number of diaphragm pumps may be provided in the microfluidic dispensing system with each of the diaphragm pumps being actuatable upon application of a corresponding pressure control pump signal, although other control arrangements may be employed, as the inventions are not limited in this respect. In addition, in one embodiment, each diaphragm pump is structured for pumping in or pumping out a fixed volume of fluid. In one embodiment, a number of supply lines are also provided, with each of the supply lines for being in fluid communication with one or more of the diaphragm pumps. For example, each supply line may be in fluid communication with a group of diaphragm pumps, where a group of diaphragm pumps may include one diaphragm pump or several diaphragm pumps. Further, each supply line may supply a corresponding ingredient to each group of diaphragm pumps simultaneously. In this regard, one (e.g., a first) supply line supplies ingredients to a first group of diaphragm pumps whereas another (e g., a second) supply line supplies ingredients to a second group of diaphragm pumps. The corresponding ingredient for each of the supply lines comes from a supply reservoir. In addition, the microfluidic dispensing system may include a plurality of nozzles with each of the nozzles being in fluid communication with a diaphragm pump. Upon application of a corresponding pressure control pump signal to the diaphragm pumps that are supplied with corresponding ingredient and that are in fluid communication with nozzles, the corresponding ingredient may be dispensed simultaneously with corresponding ingredients of other nozzles.

Alternatively, in some embodiments, one diaphragm pump may be in fluid communication with one supply line or several supply lines. In this regard, a valved configuration may be employed so that the diaphragm pump may be supplied by one supply line at a time.

In a further embodiment, a number of ingredients may be simultaneously dispensed. In this embodiment, a number of supply lines corresponds to supply reservoir that stores an ingredient. Each supply line may be used to simultaneously fill a number of corresponding diaphragm pumps that are in fluid communication with the supply lines when a fill pressure control pump signal for each corresponding diaphragm pump is appropriately applied to draw the ingredient into the pump. The ingredient for each corresponding diaphragm pump may then be dispensed through a nozzle simultaneously with other ingredients from other diaphragm pumps when a dispense pressure control pump signal for each corresponding diaphragm pump is appropriately applied.

In yet another embodiment, a fluidic connector between a supply reservoir and a supply line may be used for providing fluid communication between the supply reservoir and the supply line. The supply line may be in fluid communication with a supply inlet and associated with a magnetic inlet coupler located adjacent to or completely surrounding the supply inlet. The supply reservoir may be in fluid communication with a supply outlet and associated with a magnetic outlet coupler located adjacent to or completely surrounding the supply outlet. When the magnetic outlet coupler and the magnetic inlet coupler are magnetically coupled, a seal may be formed between the supply outlet and the supply inlet. Such a seal may prevent fluid leakage and allow effective fluid communication between the supply outlet and the supply inlet It should be understood that a supply reservoir is not a necessary aspect of the fluidic connector. It should be appreciated that fluid communication may be provided between a supply outlet and a supply inlet once the magnetic outlet coupler and magnetic inlet coupler are coupled together.

As described herein, "magnetic" may refer to any material that can exhibit magnetic properties, including ferromagnetic, electromagnetic, and paramagnetic materials. Magnetic materials do not have to exhibit magnetic properties permanently, but should have the potential to exhibit magnetic properties. Such magnetic materials that, at times, do not attract or repel other magnetic materials, may become temporary magnets. Alternatively, magnetic materials may be permanently magnetic, never losing their magnetic polarity over the working life of the magnet. Examples of suitable magnetic materials include any material or alloy with any suitably incorporated metal, such as, for example, cobalt, iron, nickel, copper, magnesium, manganese, tin, yttrium, gadolinium, dysprosium, europium, or any other appropriate metal, as the present inventions are not limited in this respect.

In another embodiment, diaphragm pumps may be supplied with corresponding ingredients for particular diaphragm pumps via aspiration through a nozzle or a tip from appropriate ingredient sources, such as, for example, wells or other reservoirs that contain ingredients. In one embodiment, tips may be suitably placed in contact with appropriate ingredient sources, so that a corresponding ingredient may be aspirated into each tip. Upon placing the tips in fluid communication with the desired diaphragm pumps, through appropriate actuation of the diaphragm pumps, ingredients corresponding to those diaphragm pumps may be drawn or aspirated into the tips. In some embodiments, actuation of the diaphragm pumps includes a pumping actuation that may be repeated as desired until the desired volume of each ingredient is reached within each tip. Once the desired volume of each ingredient is reached within each tip, the ingredient may be appropriately dispensed from the tip through appropriate actuation of each corresponding diaphragm pump.

In a further embodiment, a microfluidic dispensing system may include a microfluidic chip that includes a number of diaphragm pumps disposed on or within the microfluidic chip. Each diaphragm pump may be actuated when a corresponding pressure control pump signal is applied to the diaphragm pump. In addition, a number of tips are attached to the microfluidic chip. Each tip is in fluid communication with a corresponding diaphragm pump. Each of the corresponding diaphragm pumps, upon appropriate actuation, may provide a pressure for aspirating an ingredient into the tip. Alternatively, each of the corresponding diaphragm pumps, upon appropriate actuation, may provide a different pressure for dispensing the ingredient out of the tip.

In yet another embodiment, a number of ingredients may be appropriately dispensed from a microfluidic dispensing system that includes a microfluidic chip with a diaphragm pump and a tip attached to the microfluidic chip. In one embodiment, the diaphragm pump is actuated by applying an opening pressure control pump signal creating a negative pressure gradient within the tip and thus aspirating an air plug into the tip. The diaphragm pump may be further actuated by applying an opening pressure control pump signal creating a negative pressure gradient within the tip, so that an ingredient may be aspirated into the tip. The diaphragm may be actuated again by applying a closing pressure control pump signal creating a positive pressure gradient in the tip, so that the ingredient may be dispensed from the tip.

In some embodiments, diaphragm pumps and/or valves may be formed as multi-level structures. In some embodiments, diaphragm pumps and/or valves may be formed into groups as elastomeric clusters. In some embodiments, diaphragm pumps and/or valves may be actuated by pneumatic or hydraulic methods. Using such pneumatic or hydraulic actuation, to actuate diaphragm pumps and/or valves, the microfluidic dispensing system may include pressure ports whereby pressure within the ports causes membranes of the diaphragm pumps and/or valves to actuate such that a diaphragm pump and/or valve may open or close. Other suitable actuation arrangements may be employed, as the present inventions are not limited in this respect.

Any suitable ingredient or plurality of ingredients may be dispensed from the microfluidic dispensing system. In some embodiments, a plurality of ingredients selected to be dispensed may be one of any number of ingredients that are supplied from a number of supply reservoirs exterior to the microfluidic chip. It should be appreciated that there is no limitation to the variety of ingredients that may be supplied to supply lines, diaphragm pumps, and valves, within the microfluidic chip.

In one embodiment, discrete volumes of an ingredient to be dispensed may be predetermined by the volume of a pump space where the diaphragm pump may be filled. In one embodiment, an ingredient corresponding to a particular diaphragm pump may be dispensed repeatedly until a desired amount of ingredient is finally output.

Another embodiment relates to pump regions that are structured with diaphragm pumps of varying sizes and with valves at particular locations such that the microfluidic dispensing system has the ability to dispense discrete output volumes depending on how the diaphragm pumps and valves are actuated. When the pump space of a diaphragm pump is filled, the volume of ingredient within that pumps space will be dispensed. In some embodiments, multiple diaphragm pumps are located in a pump region, each of the diaphragm pumps having different diaphragm pump space fill sizes. As a result, a variety of discrete output volumes may be dispensed from a pump region given the discrete volume pump space sizes of each diaphragm pump.

It should be appreciated that the present inventions are not limited to the amount of discrete output volumes. Thus, in one embodiment, each pump region may provide at least two discrete output volumes from two diaphragm pumps. In another embodiment, each pump region may provide at least three discrete output volumes from three diaphragm pumps. In another embodiment, each pump region may provide at least four discrete output volumes from three diaphragm pumps. In another embodiment, each pump region may provide at least five discrete output volumes from three diaphragm pumps. In another embodiment, each pump region may provide at least ten discrete output volumes from ten diaphragm pumps. Indeed, the present inventions are not limited in having discrete sub-volume outputs, as it is possible for only one output volume to be provided as well.

In one embodiment, a diaphragm pump that is filled may subsequently dispense up to about 10 μL. It should also be understood that there is no limitation placed on the overall capacity of the pump space for each diaphragm pump, as the pump can be designed to support output volumes between approximately as small as 1 nL and as large as 10 μL. In one embodiment, a small volume output that can be dispensed from a diaphragm pump is between approximately 50 nL and approximately 500 nL. In another embodiment, a medium volume output that can be dispensed from a diaphragm pump is between approximately 500 nL and approximately 1 μL. In yet another embodiment, a large volume output that can be dispensed from a diaphragm pump is between approximately 1 μL and approximately 10 μL.

Outlets can be of any form, as the present inventions are not limited in this respect. For example, in some embodiments, outlets may include nozzles. In some embodiments, outlets may be tubes that lead to other chambers in a larger system that may include outlets themselves. In some embodiments, nozzles may include tips. In some embodiments, tips may be disposable. In some embodiments, tips may be removeably attached to the microfluidic chip. Any suitable combination of outlet arrangements may be employed, as the present inventions are not limited in this respect. For example, in one embodiment, the tips may be removable and disposable.

In another aspect, the microfluidic dispensing system is equipped with a method for cleaning. In one embodiment, purge ingredients may be run throughout supply lines, diaphragm pumps, fluid channels, valves, and outlets once or any number of times. In one embodiment, the purge fluid may flow at a high pressure to suitably wash the components. In one embodiment, diaphragm pumps and valves are appropriately actuated back and forth to suitably run purge ingredients through various channels in the system. In one embodiment, purge ingredients may be flowed several times forward and/or backward through the supply lines, diaphragm pumps, fluid channels, valves, and outlets before the next fluid ingredient is supplied for the subsequent dispense. Indeed, a combination of flowing purge ingredients through selected portions of the microfluidic chip in a reverse fashion along with flowing purge ingredients several times can also be performed before the next fluid ingredient is supplied for the next dispense. This process of filling and reverse washing can be repeatedly cycled for each of the fluid ingredients for individual supply lines, as appropriately desired.

In some embodiments, wash lines may be included in the microfluidic dispensing system for appropriate flow of purge ingredients and washing of components within the microfluidic chip. In some embodiments, wash valves associated with wash lines may also be incorporated to allow appropriate fluid communication to occur between wash lines and other components of the microfluidic chip. In some embodiments, each pump region may include one or more wash valves corresponding to diaphragm pumps and valves within the pump region. In one aspect, wash valves may provide a fluid channel to a wash line for various ingredients to be washed through a pump region and disposed of.

It should be appreciated that purge ingredients used for forward and/or reverse wash can include one or a combination of a variety of materials, such as, for example air and/or water. When ingredients to be dispensed are not suitably washed with air and/or water, then different types of purge ingredients may be used, such as acetone, ethanol, nitrogen, carbon dioxide, or other suitable gaseous or fluidic ingredients or combinations thereof.

In one embodiment, for example, pressure inlets can force purge ingredients and remaining selected ingredients through desired regions of the microfluidic chip. In another embodiment, vacuums can provide a pressure gradient, effectively pulling purge ingredients and remaining selected ingredients through desired regions of the microfluidic chip. In another embodiment, dynamic pressure variation that incorporates a combination of pressure buildup and vacuum could be used to further disturb residual fluid ingredients for more efficient washing. It should be understood that the present invention is not limited simply to reverse washing, and forward washing may also be a suitable wash method for the present invention. It should also be appreciated that washing between dispenses need not be performed, as the present inventions are not limited in this respect.

It should be understood that any diaphragm pump or valve presented herein may be controlled in any appropriate manner. In some embodiments, diaphragm pumps of a similar size may be commonly controlled. In some embodiments, each diaphragm pump may be separately controlled. Similarly, valves may also be commonly or separately controlled, as suitably desired.

A further aspect relates to the construction of diaphragm pumps and/or valves. In some embodiments, diaphragm pumps and/or valves may include physical features that improve performance, particularly with regard to mechanical flexibility and structural integrity. In some embodiments, a multi-level construction is employed for diaphragm pumps and/or valves. Multi-level diaphragm pumps and/or valves may be made of a firm but compliant material or structure with an added base structure around the diaphragm pump and/or valve providing for extra surface area, which may give rise to a more effective air-tight seal. A lip that extends upwardly may also be included in a multi-level diaphragm pump and/or valve to provide for an extra compression surface, as will be explained.

In some embodiments, diaphragm pumps and/or valves are controlled through a pressure inlet that either serves to push air against a flexible membrane, closing the diaphragm pump and/or valve, or serves to refrain from applying pressure to a flexible membrane, resulting in the opening of a diaphragm pump and/or valve. In some cases, a vacuum is applied to further facilitate opening of a diaphragm pump and/or valve, allowing for improved flow through a diaphragm pump and/or valve. It should also be appreciated that in another embodiment, a diaphragm pump and/or valve can be designed in such a way that application of pressure through an inlet to a flexible membrane could serve to open a diaphragm pump and/or valve and that not applying pressure, or applying a vacuum, through an inlet could serve to close a diaphragm pump and/or valve.

It should be understood that diaphragm pumps and/or valves may be formed out of a wide variety of suitable materials. Thus, in one embodiment, diaphragm pumps and/or valves may be made of an elastomeric material such as silicone, rubber, polyurethane, polydimethylsiloxane, or any suitable polymeric equivalent or suitable combinations thereof. In another embodiment, diaphragm pumps and/or valves may be made of a suitable rigid material, such as a metal or a ceramic, that can be actuated through any appropriate arrangement, whether electrical or mechanical in nature. If a rigid material is used, a hinge or gateway that can be opened or closed may be employed.

In another aspect, clusters of diaphragm pumps and/or valves may be formed of any suitable material and in any suitable arrangement or combinations of materials/arrangements, such as those described above with respect to the diaphragm pumps and/or valves. In addition, the clusters of diaphragm pumps and/or valves may be molded together in a single elastomeric piece. In one embodiment, discrete output volumes may be controlled as desired from one or more particular diaphragm pumps in a cluster. In such a case, clusters of diaphragm pumps and/or valves may include diaphragm pumps that open or close appropriately depending on what discrete output volume is desired.

It should be appreciated that a number of alternative embodiments exist for clustering of diaphragm pumps and/or valves. In one embodiment, a cluster of diaphragm pumps and/or valves may be used to control a particular pump region associated with an outlet (e.g., nozzle) for dispensing. In another embodiment, a cluster of diaphragm pumps and/or valves may be in fluid communication with only a portion of a pump region associated with an outlet for dispensing. In another embodiment, a cluster of diaphragm pumps and/or valves may be in communication with a number of pump regions, each of the pump regions being associated with an outlet for dispensing. It should be appreciated that any appropriate manner in which clusters of diaphragm pumps and/or valves suitable for controlling pump regions may be designed.

It should be appreciated that the above aspects may be employed in any suitable combination, as the present inventions are not limited in this respect. Also, any or all of the above aspects may be employed in a microfluidic dispensing system for use with dispensing fluid to wells of a microplate; however, the present inventions are not limited in this respect, as aspects may be used with any microfluidic dispensing systems. Various aspects and embodiments of the inventions will now be described in more detail with respect to the accompanying drawing figures. The inventions are not, however, limited to the aspects and embodiments shown.

Turning now to the figures, a perspective view of one embodiment of a microfluidic dispensing system 10 is shown in FIG. 1. The microfluidic dispensing system 10 includes a housing 12 that provides support for a microfluidic chip 100 within which a collection of structures (not shown in FIG. 1), such as for example, channels, supply lines, pumps, and valves, may be located. The housing 12 also provides structure for the microfluidic chip 100 to be manipulated, such as in allowing for movement with respect to supply sources or receiving regions. A supply reservoir 20, shown in the form of a supply bottle, located proximate to the microfluidic chip 100 is also depicted in FIG. 1. Though no connection between supply reservoir 20 and the microfluidic chip 100 is shown, it can be appreciated that any suitable conduit or arrangement may be used for an appropriate connection to be made.

FIG. 1 also shows various components, such as bottom manipulator 30, top manipulator 40, and wash station 50, for suitably interacting with the microfluidic chip 100 so as to bring about desired fluidic results. Bottom manipulator 30 and top manipulator 40 may be constructed to appropriately translate a microfluidic chip and/or a plate in any suitable direction relative to one another. In one embodiment, bottom manipulator 30 is constructed to hold a multiwell plate (not shown), from or into which ingredients may be aspirated or dispensed. Top manipulator 40 may be used to hold a microfluidic chip relative to the multiwell plate. In this example, bottom manipulator 30 may translate the multiwell plate in both a horizontal (y-axis) and a vertical (z-axis) direction as desired. In the same example, top manipulator 40 may translate the microfluidic chip in a horizontal (x-axis) direction that is perpendicular to that of the bottom manipulator. It can be appreciated that the bottom and top manipulators may be constructed to move in any suitable manner such that the microfluidic chip may be appropriately positioned relative to a receiving or supply region, such as, in this case, a multiwell plate. In some embodiments, bottom manipulator 30 may be constructed to translate in any direction while top manipulator 40 remains stationary. In some embodiments, bottom manipulator 30 and top manipulator 40 may both translate in any appropriate direction. In some embodiments, top manipulator 40 may be constructed to translate in any direction while bottom manipulator 30 remains stationary.

In some embodiments, waste or purge ingredients may exit from the microfluidic chip 100 into wash station 50. Wash station 50 may include any suitable arrangement for waste ingredients to appropriately be dispensed from the microfluidic chip 100. Waste or purge ingredients may exit from the microfluidic chip 100 via separate wash lines or outlets corresponding to pump regions associated with the chip.

Figure 2:
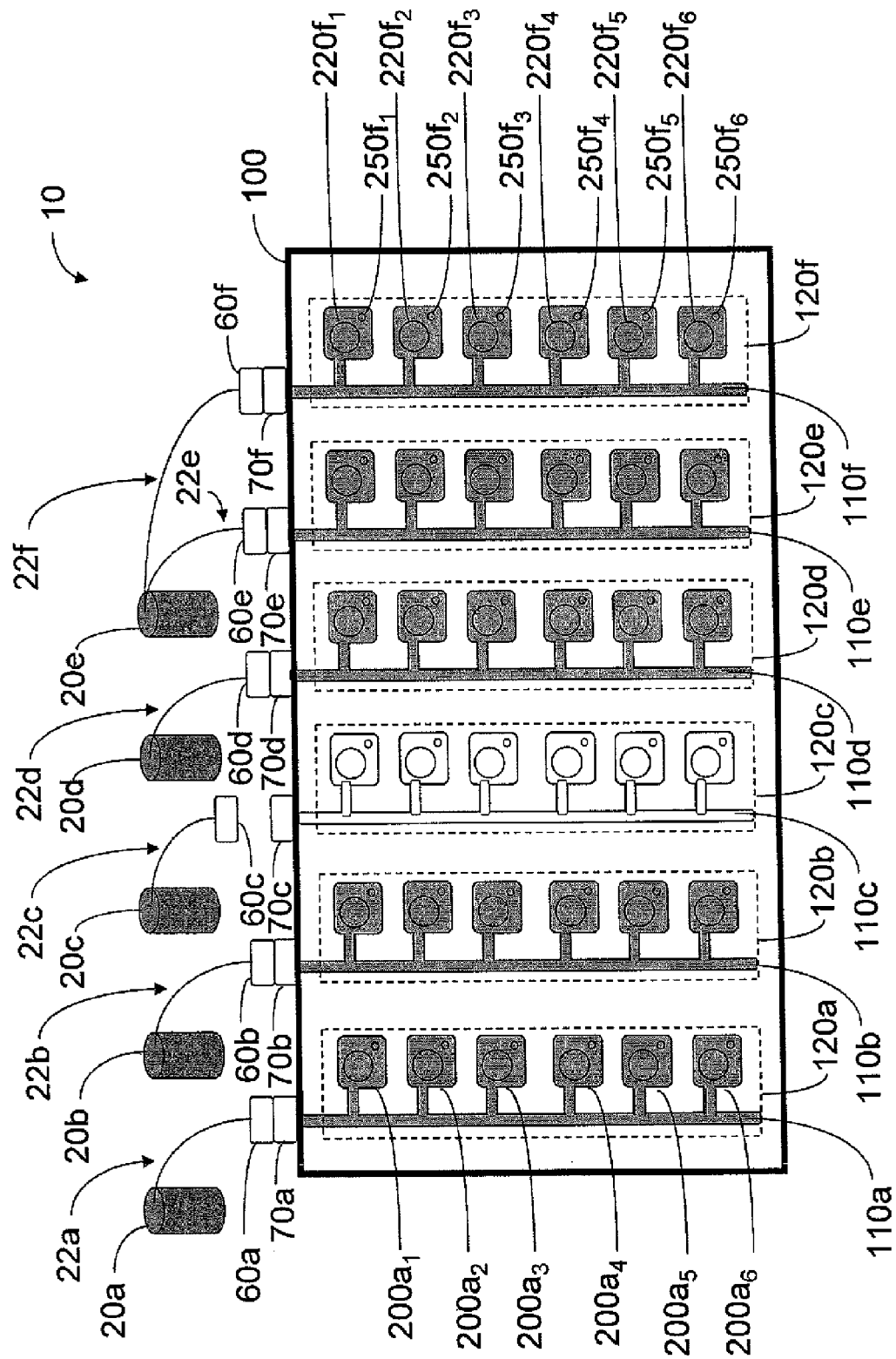
FIG. 2 is a schematic representation of a microfluidic dispensing system according to one embodiment.

FIG. 2 depicts a schematic representation of one illustrative embodiment of the microfluidic dispensing system 10. A number of ingredients are provided in corresponding supply reservoirs 20a, 20b, 20c, 20d, and 20e, and are connected to supply outlets 22a, 22b, 22c, 22d, 22e, and 22f through which ingredients may be selectively supplied for further handling in the microfluidic chip 100. Ingredients may be coupled from supply outlets 22a, 22b, 22c, 22d, 22e, and 22f to supply lines 110a, 110b, 110c, 110d, 110e, and 110f through outlet couplers 60a, 60b, 60c, 60d, 60e, and 60f and inlet couplers 70a, 70b, 70c, 70d, 70e, and 70f, respectively. In the embodiment shown, for example, an ingredient from supply reservoir 20a may enter into supply outlet 22a, which may be placed in fluid communication with supply line 110a once outlet coupler 60a and inlet coupler 70a are coupled together. Fluid communication between a supply reservoir 20 and a supply group 120 is illustrated by a shaded region, for example, supply group 120a. Similarly, in the embodiment shown, supply reservoirs 20b and 20d provide corresponding ingredients to supply outlets 22b and 22d. Upon coupling of outlet couplers 60b and 60d to inlet couplers 70b and 70d, respectively, supply outlets 22b and 22d may be placed in fluid communication with supply lines 110b and 110d, respectively. In FIG. 2, supply outlet 22c coming from supply reservoir 20c is not placed in fluid communication with supply line 110c because outlet coupler 60c and inlet coupler 70c are not coupled. In addition, as shown, supply outlets 22e and 22f are placed in fluid communication with supply lines 110c and 110f upon coupling of outlet couplers 60e and 60f, respectively, with inlet couplers 70e and 70f.

It should be understood that such a schematic representation shown in FIG. 2 is meant to depict an illustrative embodiment, and is not meant to be limiting. For example, the manner in which an ingredient may be provided from a supply reservoir 20 to a supply line 110 is not required to include a supply outlet 22, an outlet coupler 60, nor an inlet coupler 70. In some embodiments, a supply reservoir may be disposed directly on, or attached to, the microfluidic chip 100 (not shown). For example, a supply reservoir may include an appropriately sized basin for which an ingredient may be added or poured. In some embodiments, a supply reservoir may be a supply bottle, as depicted in FIG. 2. In some embodiments, a direct conduit may be implemented for placing a supply reservoir 20 in fluid communication with a supply line 110 without need for an outlet coupler or an inlet coupler.

FIG. 2 also shows one example where two supply outlets 22e and 22f are provided from one supply reservoir 20e and fluid communication is provided to supply lines 110e and 110f. Alternatively, in some embodiments, a supply reservoir 20 may employ only one supply outlet 22 to several supply lines 110. Although FIG. 2 depicts supply groups 120 of pump regions 200 as being shown in columns along the microfluidic chip 100, it can be appreciated that any appropriate configuration of pump regions may be employed corresponding to supply lines 110 within supply groups 120 of microfluidic chip 100. For example, supply groups of pump regions may be disposed as rows across a microfluidic chip. As another example, supply groups of pump regions may be disposed in groups scattered within a microfluidic chip.

The embodiment shown in FIG. 2 illustrates supply groups 120a, 120b, 120c, 120d, 120e, and 120f (depicted by dotted lines) that are associated with supply lines 110a, 110b, 110c, 110d, 110e, and 110f placed in fluid communication with pump regions that correspond to respective supply lines. For example, for supply group 120a, supply line 110a may be placed in fluid communication with pump regions $200a_1$, $200a_2$, $200a_3$, $200a_4$, $200a_5$, and $200a_6$. Furthermore, pump regions 200, as shown, include diaphragm pumps 220 and nozzles 250, corresponding to each pump region. For example, pump regions within supply group 120f may include diaphragm pumps $220f_1$, $220f_2$, $220f_3$, $220f_4$, $220f_5$, and $220f_6$. Similarly, pump regions within supply group 120f may include nozzles $250f_1$, $250f_2$, $250f_3$, $250f_4$, $250f_5$, and $250f_6$. It should be appreciated that pump regions may include more features or components than only diaphragm pumps and/or nozzles depicted in FIG. 2. For example, although not depicted in FIG. 2, diaphragm pumps may be in fluid communication with nozzles and supply lines. Such additional features will be disclosed in more detail later. It should also be appreciated that each supply group may refer to a supply line that is in fluid communication with any appropriate number of pump regions, with the capability of providing a fluid ingredient to those pump regions. In some embodiments, a supply line may provide a fluid ingredient to a single pump region. In some embodiments, using a suitable valve arrangement, a single pump region may be supplied with ingredients from a number of supply lines.

Figure 3:
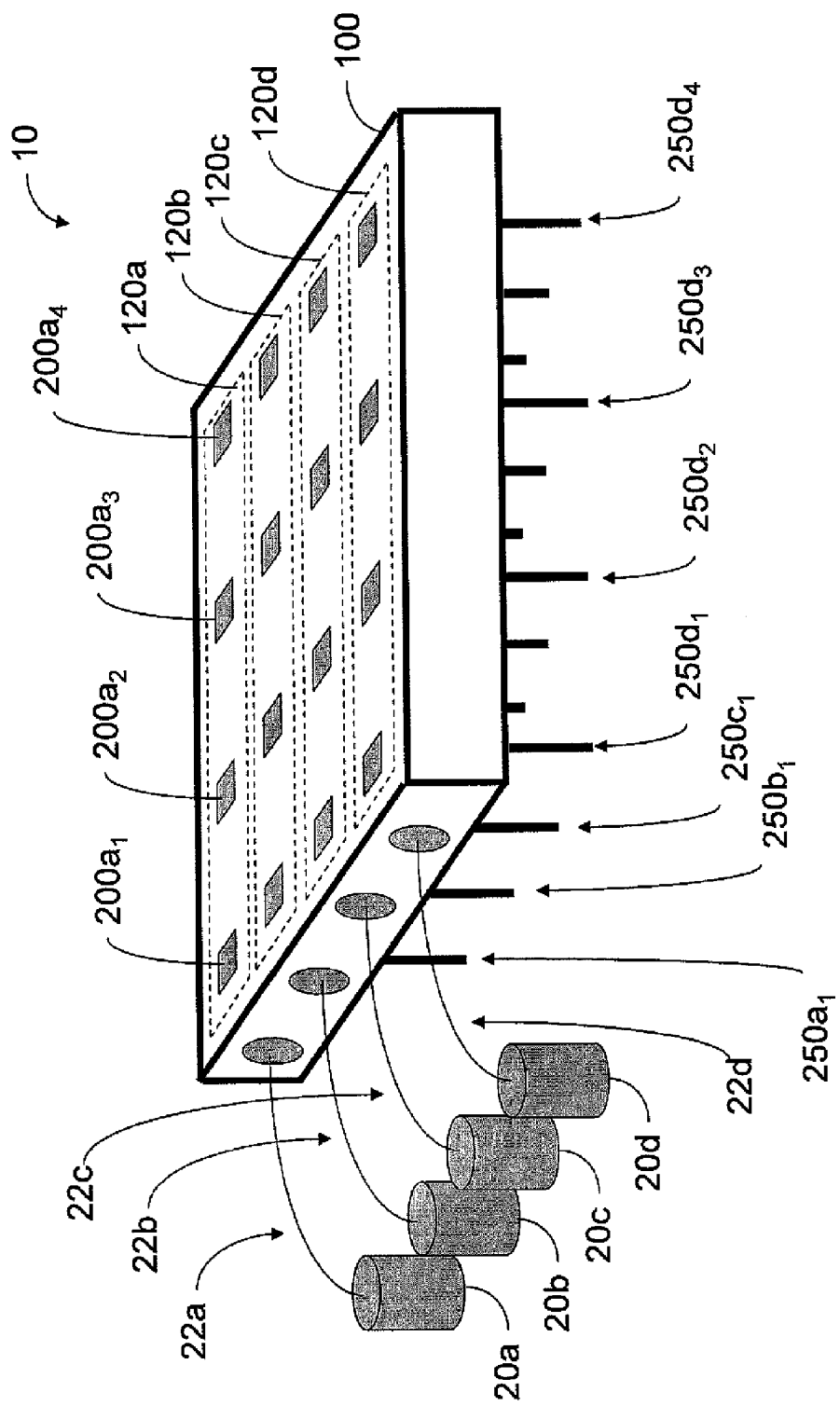
FIG. 3 is schematic perspective representation of a microfluidic dispensing system according to another embodiment.

Continuing with another schematic representation, another embodiment of microfluidic dispensing system 10 is illustrated by a perspective view shown in FIG. 3. In this embodiment, supply reservoirs 20a, 20b, 20c, and 20d provide corresponding ingredients for microfluidic dispensing system 10 through supply outlets 22a, 22b, 22c, and 22d and are placed in fluid communication with supply groups 120a, 120b, 120c, and 120d, respectively. In this embodiment, each of the supply groups, for example, supply group 120a, includes respective pump regions, for example, pump regions $200a_1$, $200a_2$, $200a_3$, and $200a_4$. Each pump region includes a corresponding nozzle 250 which acts as an outlet for dispensing and/or, as will be described further below, an ingredient source through aspiration. FIG. 3 shows nozzles $250a_1$, $250b_1$, $250c_1$, and $250d_1$, corresponding to supply groups 120a, 120b, 120c, and 120d, respectively. FIG. 3 also depicts nozzles $250d_1$, $250d_2$, $250d_3$, and $250d_4$ that correspond to supply group 120d.

As described earlier, nozzles may be formed as any suitable opening for a corresponding pump region. Ingredients may be appropriately dispensed out of nozzles corresponding to particular pump regions. In addition, ingredients may be aspirated into nozzles corresponding to particular pump regions, as appropriately desired. Nozzles may be incorporated into tips that are attached to the microfluidic chip, where tips are able to store a desired volume.

It should be appreciated that a microfluidic chip 100 may be designed so that any number of ingredients may be simultaneously supplied to pump regions via supply lines and subsequently simultaneously dispensed. It should also be understood that the ingredients to be selected from and dispensed can take on any suitable form, phase, or mixture thereof. For example, ingredients can be in liquid, gaseous, or solid phase. Furthermore, ingredients can also be a combination of one of the aforementioned phases, such as in an emulsion, immiscible mixture, or in a dissolved state.

Figure 4:
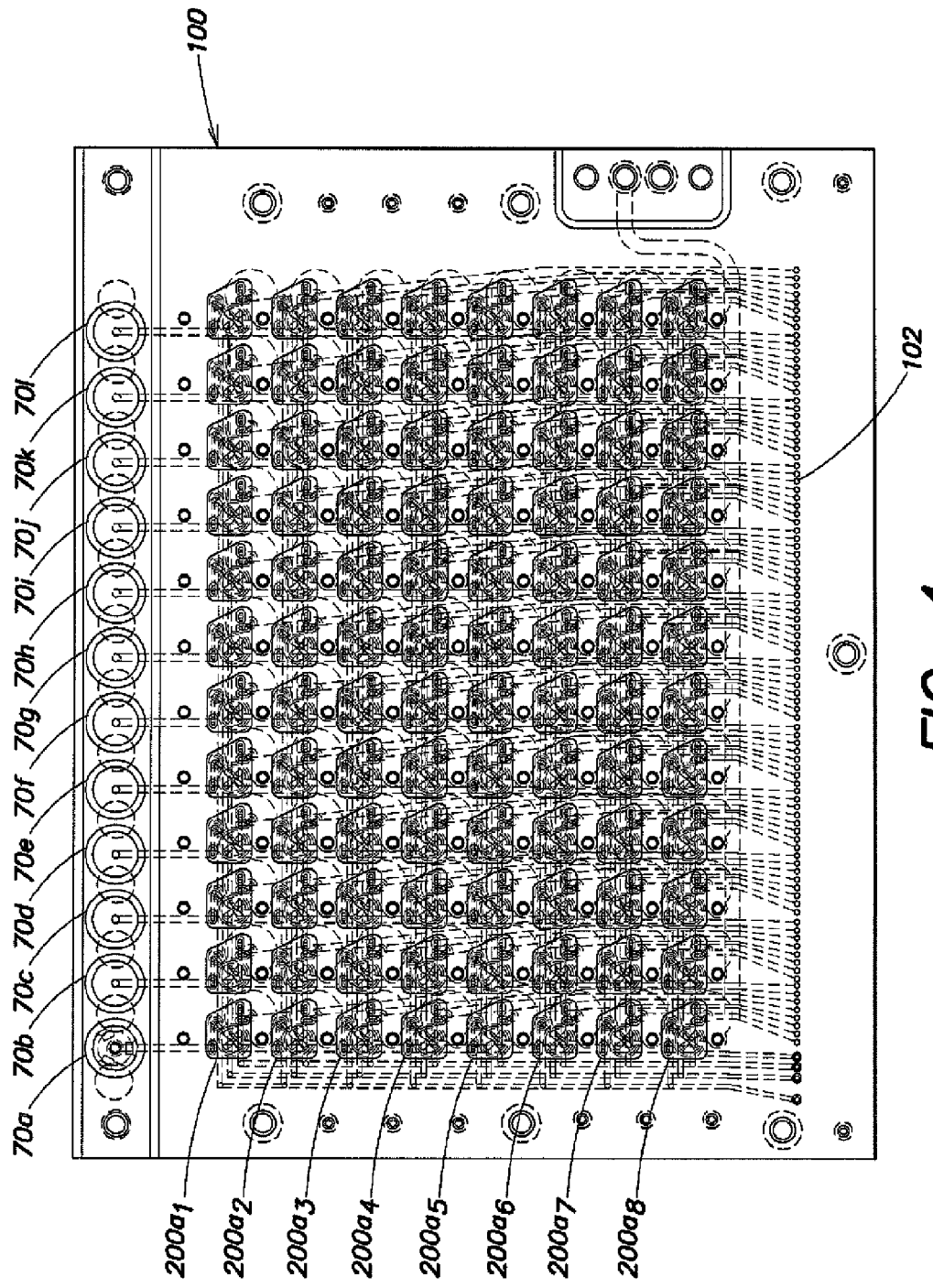
FIG. 4 is a top view of one embodiment of a microfluidic dispensing system.

FIG. 4 depicts a top view of another illustrative embodiment of microfluidic chip 100 that incorporates 96 pump regions. In this embodiment, twelve inlet couplers 70a, 70b, 70c, 70d, 70e, 70f, 70g, 70h, 70i, 70j, 70k, and 70l lead to twelve corresponding supply lines 110, each of the supply lines being in fluid communication with eight pump regions 200. As shown, for example, inlet coupler 70a is in fluid communication with supply line 110a, which in turn, is in fluid communication with pump regions $200a_1$, $200a_2$, $200a_3$, $200a_4$, $200a_5$, $200a_6$, $200a_7$, and $200a_8$. Control pressure supply ports 102 are also depicted, providing pressure control signals to diaphragm pumps and/or valves, as desired. Although in this embodiment, 96 pump regions are shown, other embodiments may be constructed with any number of pump regions, as the present inventions are not limited in this respect.

Figure 5:
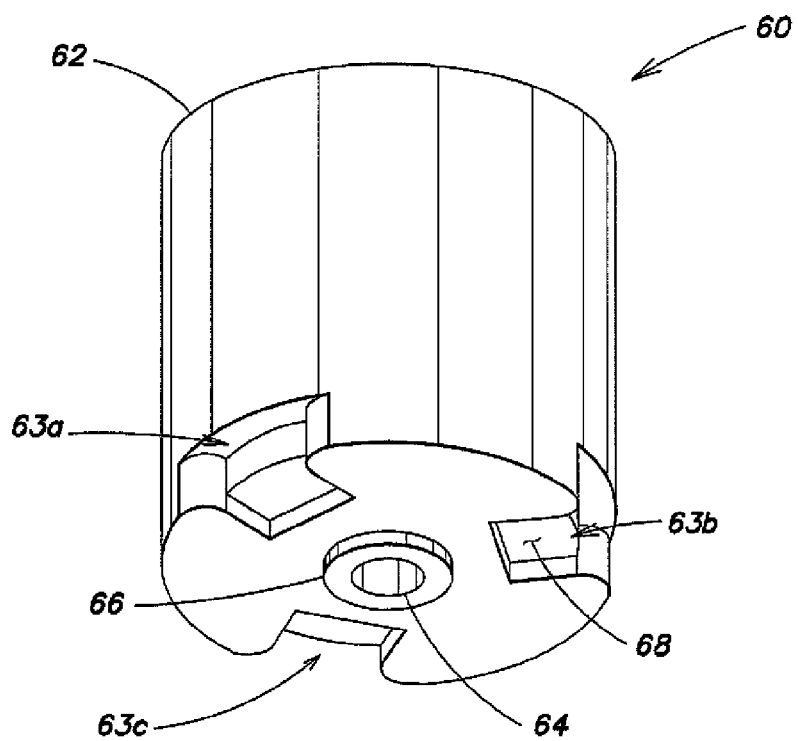
FIG. 5 is a perspective view of a magnetic outlet coupler used to connect fluid lines according to one embodiment.
Figure 6:
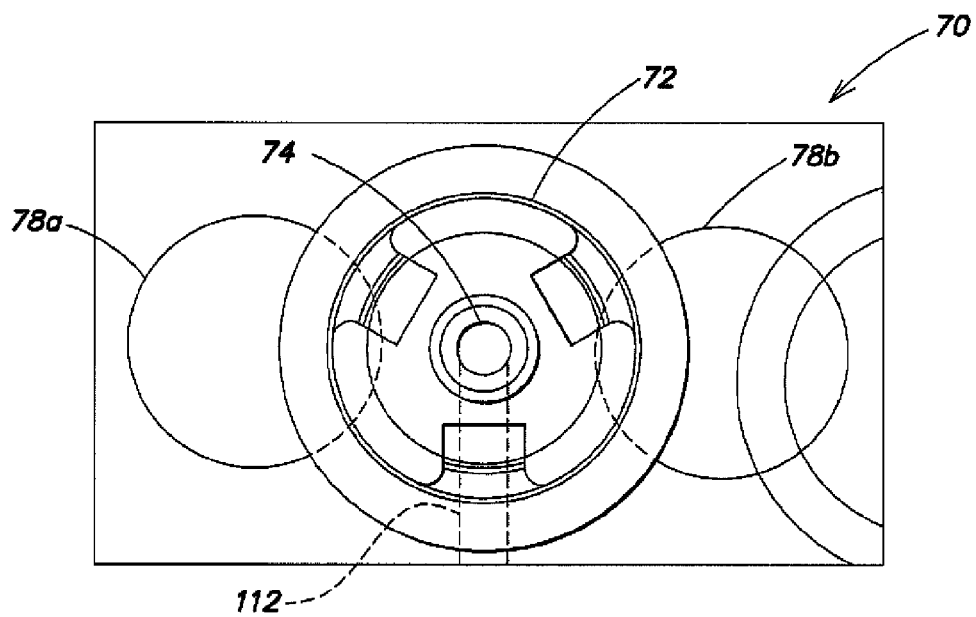
FIG. 6 is a top view of an embodiment of a magnetic inlet coupler to cooperate with the magnetic outlet coupler shown in FIG. 5.

FIGS. 5 and 6 illustrate illustrative embodiments of an outlet coupler 60 and an inlet coupler 70. The outlet coupler 60, shown in FIG. 5, is a magnetic outlet coupler, including outlet housing 62, outlet recesses 63a, 63b, and 63c, outlet conduit 64, o-ring 66, and outlet magnet 68. In this embodiment, outlet conduit 64 leads to and is in fluid communication with a supply outlet of a supply reservoir. The inlet coupler 70, shown in FIG. 6, is a magnetic inlet coupler, including inlet receiving portion 72, inlet conduit 74, and inlet magnets 78a and 78b. In the embodiment shown, outlet coupler 60 is coupled with inlet coupler 70 when outlet coupler 60 is positioned appropriately with inlet coupler 70 and a suitable seal is formed between outlet coupler 60 and inlet coupler 70. Fluid can thus flow between outlet conduit 64 and an inlet conduit 74 in a leak-free manner. In this embodiment, the inlet conduit is in fluid communication with a supply line 110 through a supply inlet 12, and the outlet conduit 64 is in fluid communication with a supply outlet of a supply reservoir. In more detail, once outlet coupler 60 couples with inlet coupler 70, the attractive force between outlet magnet 68 and inlet magnets 78a and 78b allows o-ring 66 to form a seal between outlet conduit 64 and inlet conduit 74 for leak-free fluid communication to be established between outlet coupler 60 and inlet coupler 70. Outlet housing 62 provides overall structure for outlet coupler 60 to couple with inlet coupler 70 and provide for fluid flow between the corresponding supply reservoir 20 and supply line 110.

In some embodiments, outlet recesses 63a, 63b, and 63c are provided as features resulting from manufacturing of the outlet coupler 60. In some embodiments, an alignment mechanism may be provided for a suitable fluid connection to occur between outlet coupler 60 and inlet coupler 70. It should be understood that an alignment mechanism is not required for an appropriate fluid connection to occur between outlet coupler 60 and inlet coupler 70. As discussed above, such an embodiment is meant to be an illustrative example of achieving fluid communication between a supply reservoir and a supply line, as an outlet coupler 60 and an inlet coupler 70 are not a required features of that presented herein.

Figure 7:
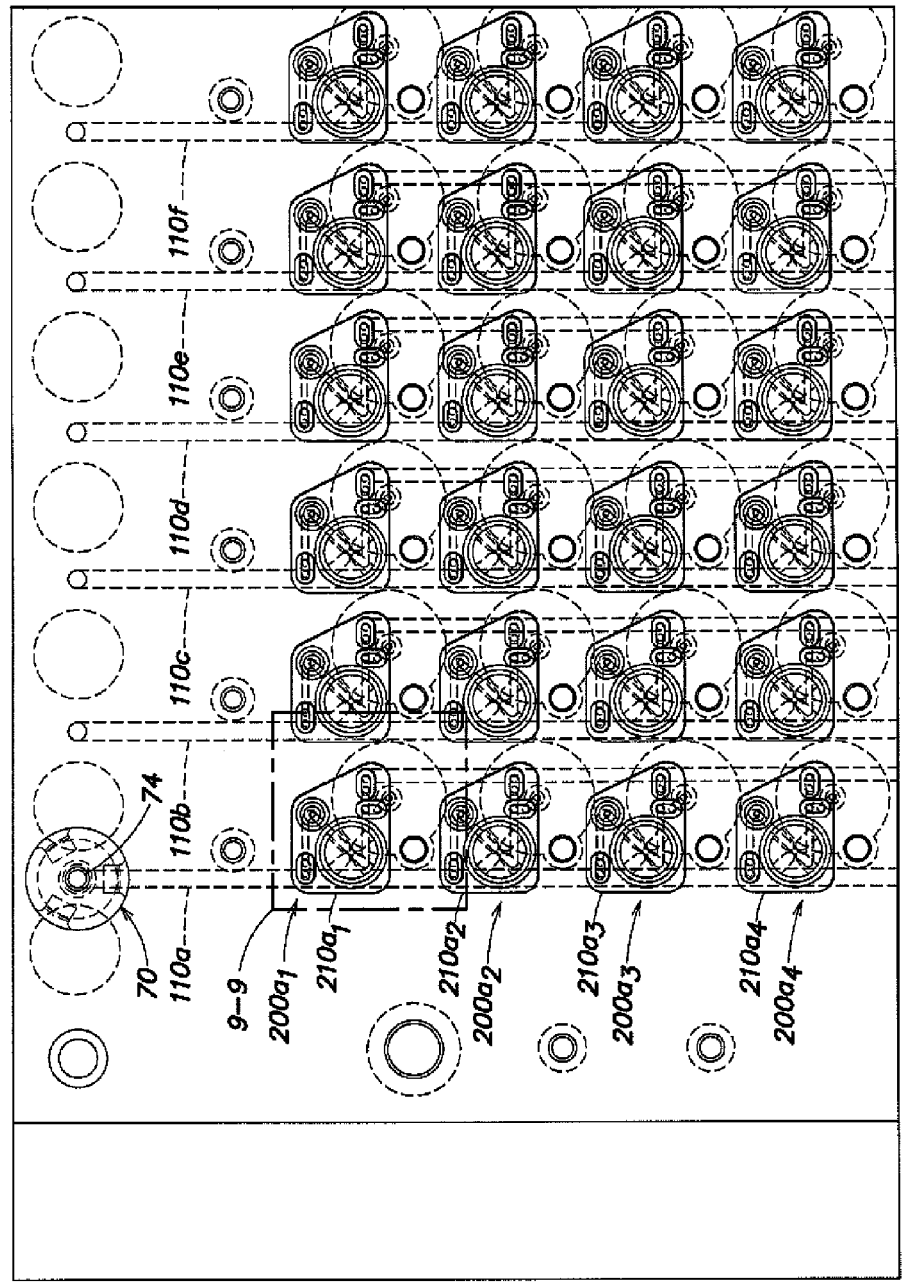
FIG. 7 is a top view of several pumping regions and fluid control clusters according to one embodiment.

FIG. 7 is an enlarged view of a portion of the microfluidic chip 100 shown in FIG. 4, showing in greater detail a number of supply lines 110a, 110b, 110c, 110d, 110e, and 110f that provide corresponding ingredients to corresponding pump regions 200. As an example, once a fluid connection is made between inlet coupler 70 and a supply reservoir 20, the ingredient may flow through inlet conduit 74 through supply line 110a, and upon appropriate actuation of diaphragm pumps, the ingredient may continue flow into pump regions $200a_1$, $200a_2$, $200a_3$, and $200a_4$. In this example, pump regions $200a_1$, $200a_2$, $200a_3$, and $200a_4$ correspond to fluid control clusters $210a_1$, $210a_2$, $210a_3$, and $210a_4$.

Figure 8:
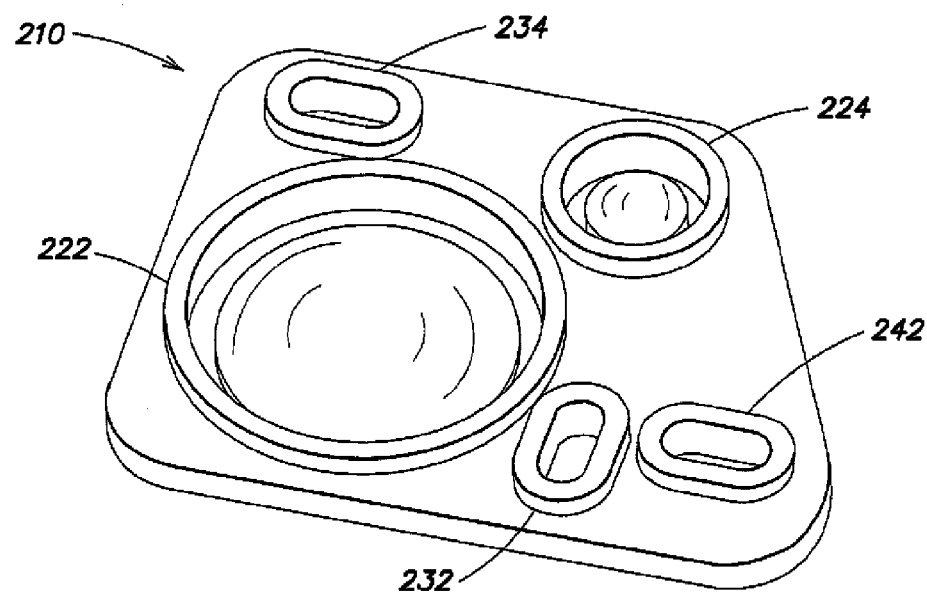
FIG. 8 is a perspective view of a fluid control cluster according to one embodiment.
Figure 9:
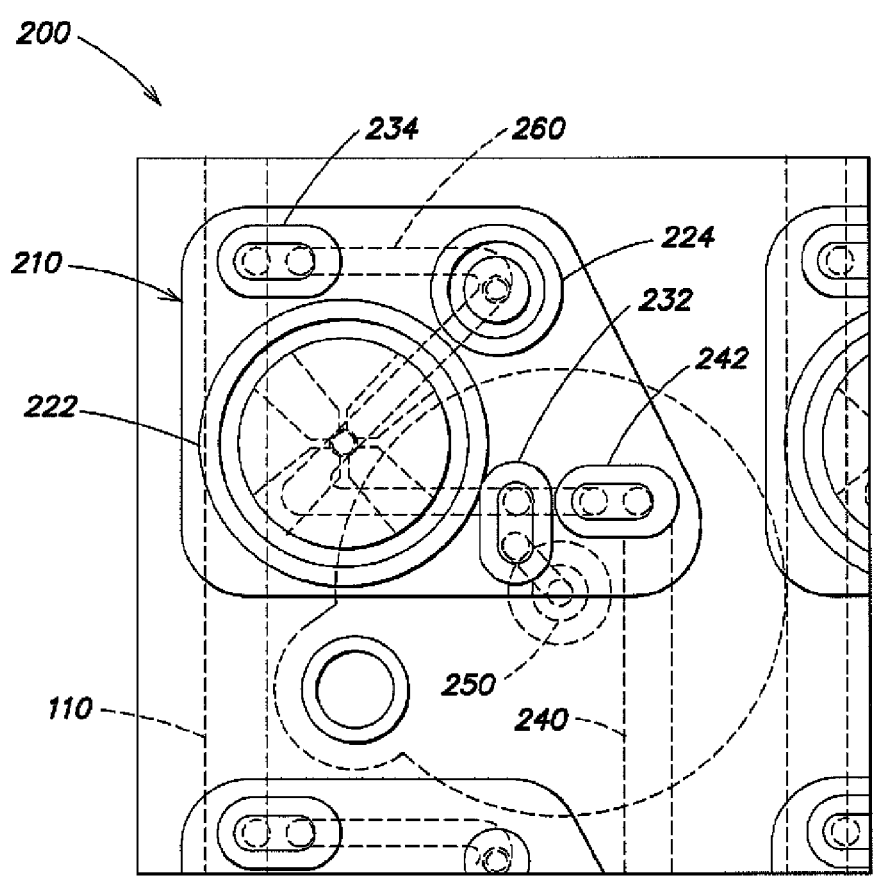
FIG. 9 is an enlarged top view of the area encircled by line 9-9 of FIG. 7.

FIG. 8 depicts a perspective view of one embodiment of a fluid control cluster 210. In this embodiment, cluster 210 incorporates structures that are also shown in FIG. 9, including a large diaphragm pump 222, a small diaphragm pump 224, a first valve 232, a second valve 234, and a wash valve 242. In this embodiment, large diaphragm pump 222 and a small diaphragm pump 224 are in between first valve 232 and second valve 234. First valve 232 is fluidly located in between the diaphragm pumps and the tip. Second valve 234 is fluidly located in between the diaphragm pumps and the supply line. It can be appreciated that a significant amount of the pressure that is present for displacing ingredient and/or system fluid through a pump region may be created by opening and closing actuation of the diaphragm pumps.

FIG. 9 illustrates a top view of a pump region 200 that incorporates a cluster 210. In addition to the structures that cluster 210 form, additional structures are also shown in pump region 200, including supply line 110, wash line 240, nozzle 250, and fluid channel 260, each of these structures providing for functionality of the pump region 200. In this embodiment, when second valve 234 is opened, ingredient is provided from supply line 110 to pump region 200, allowing for ingredient to flow through fluid channel 260 toward small diaphragm pump 224, large diaphragm pump 222, and up to first valve 232. If first valve 232 is open, then ingredient may flow directly to nozzle 250 and to wash valve 242. If wash valve 242 is open, then ingredient may then flow through wash line 240, which is provided for wash or purge ingredients. If first valve 232 is closed, then, when desired, either the small diaphragm pump 224, the large diaphragm pump 222, or both, may be actuated, suitably filling either of the diaphragm pumps by a negative pressure gradient. When dispense of the ingredient disposed in the diaphragm pumps is desired, then second valve 234 may be closed and first valve 232 may be opened. Subsequently, upon actuation of the filled diaphragm pumps by a positive pressure gradient, ingredient may be effectively pushed out of the nozzle, provided that wash valve 242 is closed.

In one embodiment, the control clusters may be molded as a unitary component. In one embodiment, the clusters are molded from an elastomeric material, such as, for example, silicone.

It can be appreciated that wash valve 242 and wash line 240 are optionally provided so that ingredients may be suitably purged from the pump regions 200. It should be appreciated that the presence of wash valve 242 and wash line 240 for each pump region is not required for suitable function of the system.

Figure 10A:
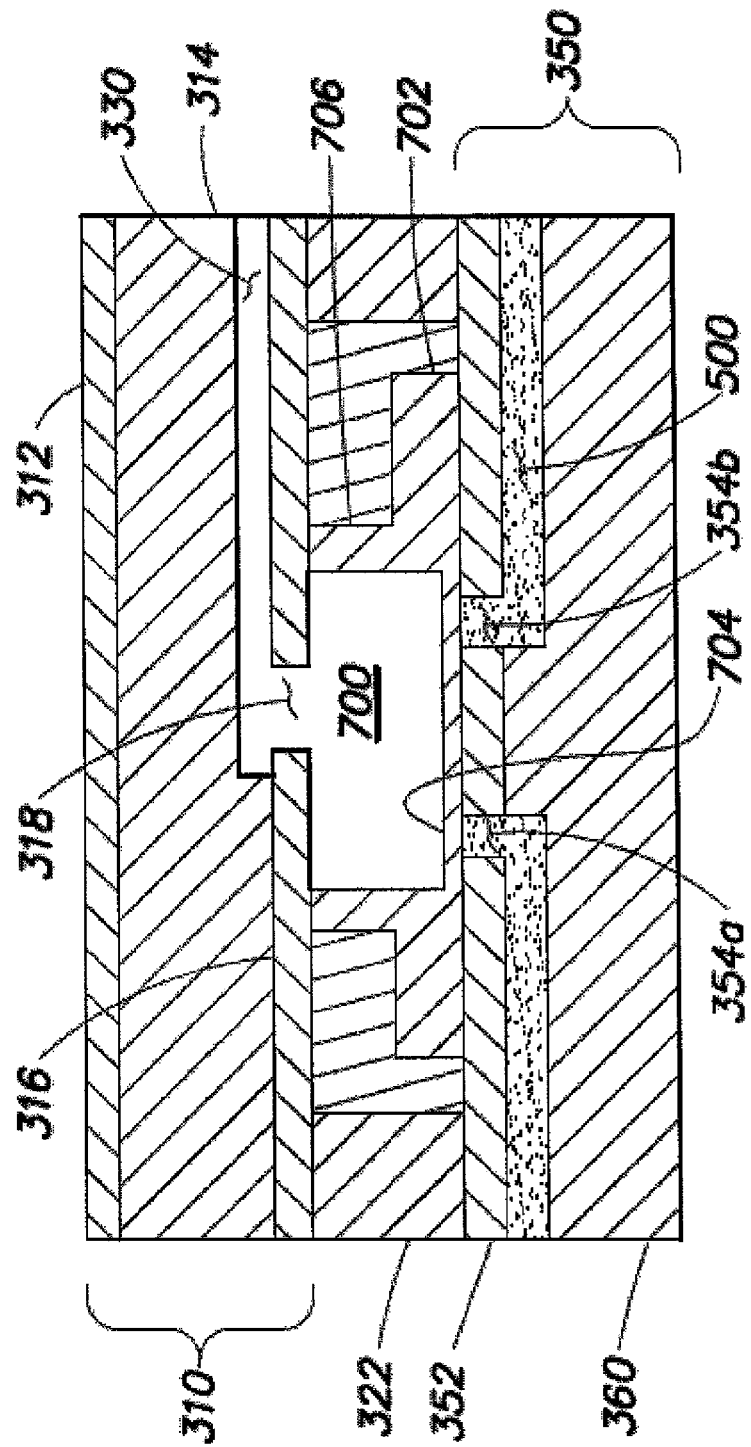
FIG. 10A is a schematic side view representation of a control valve in a closed configuration according to one embodiment.
Figure 10B:
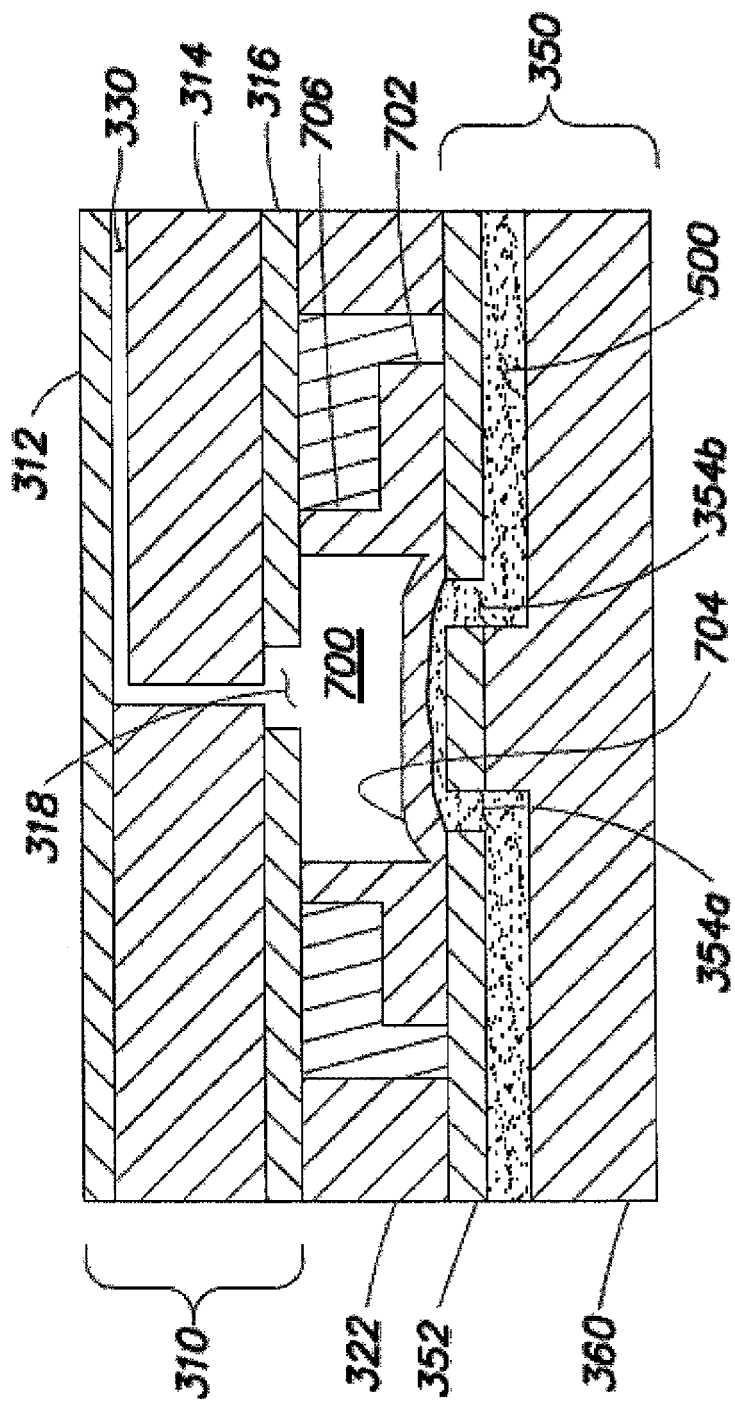
FIG. 10B is a schematic side view representation of the valve of FIG. 10A in an open configuration.

In various embodiments, microfluidic chip 100 may appropriately measure and dispense designated ingredients through designated outlets. FIGS. 10A and 10B depict a section view of an illustrative embodiment of valve disposed in microfluidic chip 100. In one embodiment, the microfluidic chip 100 is formed of two main layers: a control layer 310, and a fluid layer 350. The control layer 310 may be constructed of a control thin top layer 312, a control thick layer 314, and a control thin bottom layer 316. In one embodiment, the control thin top layer 312 may have control holes that interface with the control modules. Portions of the control thin top layer 312 appropriately seal off control channels 330 that may be located in the top side of the control thick layer 314. In this manner, control channels 330 are sealed so that pressure can be properly distributed in a suitable way. The control channels 330 may be etched in the control thick layer 314. Other suitable techniques for manufacturing channels in layer 314 may be employed, as the present invention is not limited in this respect. For example, the channels may be milled or molded in the layer. The control thin bottom layer 316 may also include control access holes 318 for control channels 330 and valves to be in communication.

It should be understood that the microfluidic chip 100 and the other layered modules are not limited to being a layered device, but could be a single monolithic piece and may be formed through suitable techniques such as molding or stereolithography techniques. Indeed, in another embodiment, the microfluidic chip 100 could also be made up of any suitable number of layers. In one embodiment, layers are held together by screws. In another embodiment, the layers are held together by a suitable adhesive material. In a different embodiment, the layers are heat sealed together. In addition, layer materials that make up a microfluidic chip are not meant to be limited to thermoplastic, but could be a number of suitable materials, for example, a metal or ceramic.

Valves can be controlled in a variety of suitable ways. In one embodiment, shown in FIGS. 10A and 10B, the valve is actuated through a single control channel 330 inlet by the application of pressure. In FIG. 10A, the valve 700 is shown in a closed state as pressure is applied through the control channel 330 that runs through a control thick layer 314 and has access through a port access hole in a control thin bottom layer 316. In FIG. 10B, the valve 700 is shown in an open state as ingredient is permitted to pass in the fluid layer 350 from one fluid access hole 354a to another fluid access hole 354b. In this case, the pressure applied from the control channel 330 is not sufficient to prevent ingredient access from one inlet to another in the fluid layer 350. In another embodiment, a vacuum is applied through control channel 330, allowing for greater flow of ingredient from one inlet to another.

In one embodiment, the valve 700 is disposed between the control layer 310 and the fluid layer 350, serving as a conduit for communication to occur between the two layers. The valve is constructed as a molded silicone valve 700 and includes a base 702, a valve membrane 704, and a valve lip 706. The base 702 provides a surface for compression against a fluid thin layer 352, making an airtight seal supported by spacers 322. In one embodiment, spacers 322 are slightly shorter than the valve lip 706. In one embodiment, the base 702 is thicker than the membrane 704. The added thickness may aid in preventing the valve membrane 704 from stretching and skewing. In one embodiment, the base 702 may be approximately 300 μm thick.

In a closed state, valve membrane 704 prevents a fluid ingredient from passing through from one fluid access hole 354a to another fluid access hole 354b when sufficient pressure to close the membrane is applied through the control channel 330, shown in FIG. 10A. By the same manner, in an open state, valve membrane 704 allows for a fluid ingredient to pass through from one fluid access hole 354a to another fluid access hole 354b when the pressure to close the membrane is not great enough, as shown in FIG. 10B. In one embodiment, the valve membrane 704 may be approximately 100 μm thick.

Valve lip 706 may provide added stability once pressure is applied to the system. The valve lip extends upward from the valve membrane and in one embodiment is about 200 μm tall above the base 702. The relatively large height as compared to the valve membrane thickness may also compensate for variances in tolerance between the layers of the fluid chip. In this manner, when the device is assembled and the layers are brought together, any fluctuation in layer thickness (or even lip height itself) is accommodated due to the amount the lip can deflect due to its relatively tall height.

Fluid flow may be controlled using any suitable arrangement. In some embodiments, fluid flow is controlled with solenoid actuated valves. In some embodiments, different groups of diaphragm pumps and/or valves on a microfluidic chip 100 may share control from single solenoid control sources. In some embodiments, individual diaphragm pumps and/or valves on a microfluidic chip 100 may be individually controlled from single solenoid control sources. In some embodiments, control pressure pump signals may be used in controlling diaphragm pumps. In some embodiments, control pressure valve signals may be used in controlling valves. Control pressure may be in the range of 20-30 PSI, and in one embodiment, is approximately 25 PSI.

Turning now to FIGS. 11A and 11B, one illustrative embodiment of a diaphragm pump 900 will now be described. The diaphragm pump 900 may have a molded multi-level construction that includes a base 902, a flexible membrane 904, and a lip 906. Similar in construction to that of valve 700, the base 902 may provide a compression surface against a fluid thin layer 352, adding stability to the diaphragm pump 900 while allowing for an airtight seal to be formed. Also similar in construction to that of valve 700, the lip 906 may extend upward from between the base 902 and the flexible membrane 904, allowing diaphragm pump 900 to be anchored in place. The lip also provides a seal around its perimeter. In addition, flexible membrane 904 may include two regions, a raised thickness portion 905 in substantially the center of the membrane, and a thinner portion 903 that substantially surrounds the thicker portion 905. When the flexible membrane 904 of the diaphragm pump 900 is actuated in a direction away from the fluid layer 350, the thicker portion 905 of the flexible membrane 904 may be pushed up against a rigid upper stop constraint, for example control thin bottom layer 316, which may result in a more consistent metering volume to eventually be expelled from the pump 900.

In the embodiment illustrated, the base 902, the flexible membrane 904, and the lip 906 are integrally formed together. In this case, the base 902, the flexible membrane 904, and the lip 906 are molded together as one unitary piece with the lip 906 disposed in between the base 902 and the flexible membrane 904. In addition, the lip 906 is of a greater thickness than the base 902 and the flexible membrane 904. It should be understood that it is not a necessary requirement for the base 902, the flexible membrane 904, and the lip 906 to be integrally formed together as, in other embodiments, one of the components may be formed separately from the other two. In some embodiments, all three of the components may be formed separately from the others.

In various embodiments, the thickness of the thicker portion 905 of flexible membrane 904 may vary. In some cases, the thickness of the thicker portion 905 may vary according to the volume that is desired for a pump to dispense. In some embodiments, there is no thicker portion, as the thickness of the flexible membrane 904 may be substantially uniform across the surface, i.e., the thicker portion 905 is substantially the same thickness as the thinner portion 903. In other embodiments, the thickness of the thicker portion 905 may be as tall as the lip 906 that surrounds the flexible membrane 904. In this regard, if the thicker portion 905 is as tall as the lip 906, extending from the fluid layer 350 to the control layer 310, then the membrane 904 would not be able to substantially actuate without severe deformation. However, if the height of the thicker portion 905 is less than the height of the lip 906, then upon membrane actuation toward the control layer 310, a small volume of fluid could be temporarily stored between the fluid layer 350 and the membrane 904. If the height of the thicker portion 905 is slightly less than the height of the lip 906, then if the membrane is actuated toward the control layer 310, then a smaller volume could be metered out from a diaphragm pump 900 than if the thicker portion 905 is significantly shorter than the height of the lip 906. In various embodiments, the thicker portion 905 may range from approximately 100 microns thick to approximately 500 microns thick. In some embodiments, the thicker portion 905 may be approximately 400 microns thick. In other embodiments, the thicker portion 905 may be approximately 220 microns thick.

The thicker portion 905 may also be shaped in any suitable form. In some embodiments, the thicker portion 905 may be substantially rectangular in shape. In other embodiments, the thicker portion 905 may be substantially trapezoidal in shape. In further embodiments, the thicker portion 905 may be substantially shaped as a parallelogram.

In another aspect, the thinner portion 903 may allow for the flexible membrane 904 to deflect upon actuation, for example, through application of a pressure or vacuum from the control layer 310. In this respect, the distance of the thinner portion 903 of the membrane 904 that exists between the lip 906 and the thicker portion 905 may be suitably determined such that excessive stresses and/or slack incurred by the thinner portion 903 may be largely avoided upon membrane actuation. In this regard, the distance of the thinner portion 903 from lip 906 to thicker portion 905 may be large enough such that the thicker portion 905 may reach the relatively rigid back stop without excessive stretch placed on the thinner portion 903. On the other hand, the distance of the thinner portion 903 from lip 906 to thicker portion 905 may also be limited enough so that the flexible membrane 904 does not awkwardly deform from excessive slack. In some embodiments, the distance of the thinner portion 903 of the flexible membrane 904 from lip 906 to thicker portion 905 is approximately the thickness of the thinner portion 903 of the membrane 904. In other embodiments, the distance of the thinner portion 903 of the flexible membrane 904 from lip 906 to thicker portion 905 is approximately the thickness of the thicker portion 905. In further embodiments, as previously described, there is no thicker portion 905 of the flexible membrane 904, resulting in a distance of the thinner portion 903 of the membrane 904 running from one side of a lip 906 to another side of a lip 906.

In other aspects, a thicker membrane portion 905 may also aid in lowering the possibility of having fluid become caught at the side edges 903 of the flexible membrane 904. In this respect, for some embodiments, the membrane 904 may be designed such that the thinner side edges 903 of the membrane 904 may deform more readily than the thicker portion 905. In different embodiments, as previously mentioned, the thicker portion 905 may be formed out of a substantially more rigid material than the more flexible regions of the membrane 904. It can be appreciated that for the diaphragm pump 900 to suitably function, it is not a requirement for the flexible membrane 904 to be of varying thickness. It can also be appreciated that for a valve 700 to suitably function, a thicker membrane portion 905 may also be incorporated into the flexible membrane 904.

FIG. 11A depicts diaphragm pump 900 in an empty state where a seal is formed between the membrane 904 and the fluid thin layer 352. In this respect, enough force is exerted on the membrane 904 and/or by the membrane 904 so as to prevent a fluid ingredient 500 from passing from the fluid channel 502 through a fluid access hole 954. FIG. 11B shows diaphragm pump 900 in a fill state where the seal between the membrane 904 and the fluid thin layer 352 has been released and a fluid ingredient 500 is permitted to pass from fluid channel 502 through fluid access hole 954. In this respect, a pump space 910 with fluid temporarily stored within is formed as the membrane 904 is pushed up against the control thin bottom layer 316 which acts as a rigid back stop, limiting excessive membrane deflection. For the embodiment depicted, the rigid back stop creates a constraint that allows for the amount of fluid temporarily stored within pump space 910 to be well controlled. Accordingly, aspects of pump 900 may be designed to consistently meter out precise volumes of fluid according to the pump space 910 that may be filled as desired.

Diaphragm pump 900 may be controlled through application of pressure, where a fluid, e.g., air, may be pushed against a flexible membrane 904 so that fluid ingredient 500 may be expelled out of the pump 900. In various embodiments, it is possible for a lack of pressure to be applied to the flexible membrane 904, allowing fluid to flow through a fluid access hole 954 immediately underneath the membrane 904. In another embodiment, a vacuum may be applied to the flexible membrane 904, allowing for fluid to more easily flow into a pump space 910. It should be appreciated that in different embodiments, the opposite control effect could occur, where the diaphragm pump 900 may be designed such that application of pressure through a control port to the membrane 904 could serve to allow fluid to be received into a pump space 910, and that not applying pressure, or applying a vacuum, through a control port could serve to expel material out of the pump space 910.

In addition, similar to the described valve 700, the diaphragm pump 900 may be formed out of a wide variety of suitable materials. In some embodiments, valves 700 and/or diaphragm pumps 900 may be formed out of an elastomeric material such as silicone, rubber, polyurethane, polydimethylsiloxane, fluoropolymer (e.g., perfluoroelastomers such as Kalrez®), or any suitable polymeric equivalent or suitable combinations thereof. In other embodiments, the material which valves 700 and/or diaphragm pumps 900 are made out of are substantially solvent resistant. In further embodiments, the valves may be made of a suitable rigid material, such as a metal or a ceramic, that can be actuated through any appropriate arrangement, whether electrical or mechanical in nature. If a rigid material is used, a hinge or gateway that can be opened or closed may be employed. In yet more embodiments, different parts of valves 700 and/or diaphragm pumps 900 may be formed out of a variety of materials. As a non-limiting example, flexible membrane 904 may be formed out of one material, or alternatively, may be formed out of a plurality of materials. In this respect, a thicker portion 905 may incorporate a material that may be substantially different and/or substantially more rigid, for example, than other parts of the flexible membrane 904.

FIG. 11A depicts one embodiment of a diaphragm pump 900 in an emptied state where the flexible membrane 904 forms a seal with the fluid thin layer 352, substantially preventing fluid from entering into a pump space 910 above the fluid layer 350. In some embodiments, pressure may be appropriately applied through a control channel 330 that may run through a control thick layer 314, being in communication with a control access hole 318 in a control thin bottom layer 316. When the diaphragm pump 900 empties, fluid may be suitably pushed out from its pump space 910 into a fluid channel 502.

FIG. 11B depicts another embodiment of a diaphragm pump 900 in a fill state where the flexible membrane 904 is brought towards the more rigid control thin bottom layer 316 and fluid enters into the pump space 910 from the fluid channel 502. In this respect, a vacuum, or lack of pressure, may be applied through a control channel 330 that may run through a control thick layer 314, in communication with a control access hole 318. When the diaphragm pump 900 fills, fluid may be suitably pulled into its pump space 910.

As previously described, it is possible for flexible membrane 904 to be controlled by the application of pressure or vacuum through a control channel 330 where applying pressure may allow the membrane to close, empty its pump space 910, and/or stay closed. On the other hand, applying a vacuum may result in the flexible membrane 904 opening and filling its metering chamber 910 and/or remaining open. In some embodiments, the control access hole 318 may be positioned off center towards the edge of the membrane 904 such that when the diaphragm pump 900 is in its fill or open state, the membrane 904 does not block control access hole 318. It is also possible for an off centered control access hole 318 to help ensure that the diaphragm pump 900 delivers an appropriate volume of fluid by lowering the chance that the membrane 904 prematurely blocks passage of fluid to the fluid access hole 954. It should be understood that it is not required for the control access hole 318 to be positioned off center with respect to the membrane 904.

In addition, an appropriate system fluid may be employed throughout the microfluidic chip or only in desired pump regions prior to introducing desired ingredients into supply lines of the microfluidic chip. The system fluid may serve to prime fluid channels within pump regions along with diaphragm pumps and valves before ingredients enter in to the channels. A system fluid may be useful to ensure that flow through channels of a pump region, along with diaphragm pumps and valves, is even. In some cases, when a system fluid does not have relatively similar characteristics (e.g., viscosity, density) as an incoming ingredient, uneven flow through elements of a pump region may occur. When uneven flow through elements of a pump region does occur, inconsistent dispensing or partially blocked fluid channels may arise. In some cases, uneven flow through fluid channels may produce air bubbles along a fluid channel or even in pump spaces associated with diaphragm pumps. As a result it may be advantageous to prime pump regions and/or supply lines of a microfluidic chip with a suitable system fluid. A system fluid may be any appropriate fluid, such as for example, water, saline, dimethyl sulfoxide, alcohol, any other suitable solution, or mixtures thereof.

FIGS. 12A-12F depict, for one embodiment, operation of a diaphragm pump 900 surrounded by a valve 901a on one side and a valve 901b on the other side. In this respect, fluid ingredient 500 is transported via fluid channel 502a from one side through valve 901a to fluid channel 502b, metered into and expelled out of diaphragm pump 900 toward the other side through valve 901b toward fluid channel 502c. Control is provided through control layer 310 via positive and negative pressure control and fluid access occurs in fluid layer 350. Diaphragm pump 900 and valves 901a and 901b are positioned in between control layer 310 and fluid layer 350. In this embodiment, valves 901a and 901b, and diaphragm pump 900 are integrally connected and formed of the same material. It should be understood that diaphragm pumps 900 and/or valves 901a and 901b are not required to be formed of the same material nor are diaphragm pumps 900 and/or valves 901a and 901b required to be connected.

It should also be understood that even though control thin bottom layer 316 and fluid thin layer 352 are each depicted to be one unitary piece, none of the layers described herein are required to be a unitary piece as such. For example, pieces of layers could be positioned relative to one another, in any appropriately functioning combination. Furthermore, as described above for valve 700, for added support, spacers 322 may be suitably positioned between control layer 310 and fluid layer 350.

In FIG. 12A, while fluid channels 502a, 502b, and 502c are primed with fluid ingredient 500, both valves 901a and 901b along with diaphragm pump 900 are closed. In this respect, pressure may be applied from control channel 330a through control access port 318a such that the flexible membrane 904a of valve 901a forms a seal with the fluid thin layer 352, preventing fluid to flow between fluid access ports 354a and 354b. Similarly for valve 901b, pressure may be applied from control channel 330b through control access port 318b such that the flexible membrane 904b forms a seal with the fluid thin layer 352, preventing fluid to flow between fluid access ports 354c and 354d. As fluid flow is impeded between valves 901a and 901b, diaphragm pump 900 also remains in an emptied configuration. In this case, pressure may be applied from control channel 330c through control access port 318c such that the flexible membrane 904c forms a seal with the fluid thin layer 352, preventing fluid to flow through fluid access port 954.

FIG. 12B shows valve 901a in an open state, allowing fluid ingredient 500 to flow from fluid channel 502a to fluid channel 502b through fluid access holes 354a and 354b. In this respect, pressure that was previously applied from control channel 330a to valve 901a is released and application of a vacuum allows for the seal between flexible membrane 904a and the fluid thin layer 352 to be released, permitting fluid to flow through valve 904a. It can be appreciated that a vacuum is not required for fluid to flow through valve 904a as in some embodiments, a simple decrease in the pressure applied through control channel 330a may at least partially release the seal between membrane 904a and fluid thin layer 352. In this case, a seal between the membranes of diaphragm pump 900 and valve 901b with the fluid thin layer 352 still remains as pressure may be applied through control channels 330b and 330c.

FIG. 12C shows diaphragm pump 900 entering into a fill state as fluid ingredient 500 from fluid channel 502b is drawn into the pump space 910 through fluid access hole 954 from the direction of fluid channel 502a as a vacuum is applied through control channel 330c. In this regard, the thicker portion 905 of flexible membrane 904c is substantially prevented from further deformation as the membrane 904c may, for example, come into contact with the relatively rigid control thin bottom layer 316. As a result, the volume of fluid ingredient 500 pulled into the pump space 910 may be consistent with each fill state. It can be appreciated that a vacuum is not required for fluid to flow up into the pump space of diaphragm pump 900 as in some embodiments, a simple decrease in the pressure applied through control channel 330c may at least partially release the seal between membrane 904c and fluid thin layer 352. At this point, as depicted in FIG. 12C, for some embodiments, control channels 330a and 330c apply a vacuum to valve 901a and diaphragm pump 900, respectively, releasing the seal between flexible membranes 904a and 904c and fluid thin layer 352. At the same time, control channel 330b applies a pressure to valve 901b, maintaining the seal between flexible membrane 904b and fluid thin layer 352.

FIG. 12D shows valve 901a in a closed state, preventing fluid flow between fluid channels 502a and 502b. In this respect, pressure is applied from control channel 330a so that a seal may be formed between flexible membrane 904a and fluid thin layer 352. On the other hand, valve 901b is depicted in an open state where a vacuum is now applied from control channel 330b so that the seal between flexible membrane 904b and fluid thin layer 352 may be released, allowing fluid to flow between fluid channels 502b and 502c through fluid access holes 354c and 354d. Diaphragm pump 900 remains in a fill state, with vacuum application remaining via control channel 330c. Similar to that described above, it can be appreciated that a vacuum is not required for fluid to flow through valve 901b as in some embodiments, a simple decrease in the pressure applied through control channel 330b may at least partially release the seal between membrane 904b and fluid thin layer 352.

FIG. 12E depicts valve 901a remaining in a closed state, with positive pressure continuing to be applied from control channel 330a, maintaining the seal between flexible membrane 904a and fluid thin layer 352, and resulting in prevention of fluid flow between fluid channels 502a and 502b. Valve 901b also remains in an open state with a vacuum continued to be applied from control channel 330b for the seal between flexible membrane 904b and fluid thin layer 352 to remain released, allowing fluid flow to occur between fluid channels 502b and 502c. However, diaphragm pump 900 actuates to an empty state from pressure applied through control channel 330c where fluid that had previously been in the pump space 910 is pushed out through fluid access hole 954 to fluid channel 502b and in a direction toward valve 901b. At this point, because valve 901b is open, allowing fluid to flow through to occur, fluid ingredient 500 is able to be transported from fluid channel 502b to fluid channel 502c through fluid access holes 354c and 354d through force applied from the membrane 904c of diaphragm pump 900.

FIG. 12F depicts valves 901a and 901b both in a closed state with pressure applied from control channels 330a and 330b, respectively, on to the flexible membranes 904a and 904b. Diaphragm pump 900 is also shown in an empty state where pressure is applied from control channel 330c on to flexible membrane 904c. It should be understood that as fluid flow depicted in FIGS. 12A-12F occurs from fluid channel 502a to fluid channel 502c, in this embodiment, depending on how valves 901a and 901b and diaphragm pump 900 are operated, fluid flow could also be controlled from fluid channel 502c to fluid channel 502a and back again.

It should be appreciated that various arrangements and combinations of valves and diaphragm pumps as discussed above may be constructed in a dispensing device for precise control of fluid flow direction and volume to occur as desired. In this respect, valves on either side of a diaphragm pump 900 may control when fluid is to be dispensed and the diaphragm pump 900 may serve to meter and push out a suitable amount of fluid through the fluid channels and out of the device when valves and other parts of the device are appropriately actuated. In this regard, when incorporated into different aspects of the overall microfluidic dispensing device, depending on how diaphragm pumps are constructed, dispense volumes may range widely from approximately 10 nanoliters to approximately 100 microliters. In some embodiments, dispense volumes may be approximately 100 nanoliters. In other embodiments, dispense volumes may be approximately 3 microliters.

Although in the embodiments described, the diaphragm pumps and/or valves are actuated through the application of pressure, the inventions are not limited in this regard. Thus, in another embodiment, the diaphragm pumps and/or valves are actuated through electrical switching means. In another embodiment, diaphragm pumps and/or valves are actuated through mechanical switching. In various embodiments, diaphragm pumps and/or valves are actuated pneumatically and/or hydraulically. In other embodiments, diaphragm pumps and/or valves are actuated through use of piezoelectric materials.

In addition, any number of diaphragm pumps and valves may be employed in any suitable configuration. In some embodiments, any number of diaphragm pumps of suitable size may be included along a fluid channel in a pump region with valves at the ends of the fluid channel. For example, instead of two diaphragm pumps included along a fluid channel within a pump region with valves at the ends of the fluid channel, one diaphragm pump may be incorporated. Or alternatively, three or more diaphragm pumps may be incorporated along a fluid channel within a pump region with valves at the ends of the fluid channel.

In addition, valves may be incorporated in between diaphragm pumps along a fluid channel within a pump region, as desired. For example, for the two diaphragm pump arrangement, a valve may be incorporated along the fluid channel between the diaphragm pumps.

Furthermore, any suitable number of fluid channels may extend from diaphragm pumps. For example, a fluid channel within a pump region may extend from one diaphragm pump into two or more valves rather than a single valve.

In one embodiment, the valve structure 700 that has been described above may also be used as a diaphragm pump in facilitating transport of fluid back and forth through fluid access port holes. More specifically, with such a pump, upon membrane actuation, fluid may travel back through the same port from which the fluid entered in. It should be understood that the valve structure described previously may be referred to as a diaphragm pump, as the manufacture of the structures may be substantially similar, yet slight differences may exist in operation between an article with a flexible membrane that is used as a valve and/or used as a diaphragm pump. For example, the number of fluid access ports that contact the structure from the fluid layer 350 may vary. In some embodiments, one port hole may serve as both an inlet and outlet for a diaphragm pump. In other embodiments, a plurality of ports, serving as inlets and/or outlets may be employed. Indeed, when manufactured, a valve may functionally be used as a diaphragm pump, and conversely, a diaphragm pump may be used as a valve.

In addition, diaphragm pumps may also serve as metering chambers themselves, where fluid that is to be dispensed from a microfluidic assembly at a precise amount may be temporarily stored within a pump space. In this regard, valves and diaphragm pumps may be used in whatever suitable fashion to control efficient and accurate dispensing of a multiple of ingredients as desired.

In embodiments described, ingredients have been provided to diaphragm pumps of pump regions within a microfluidic chip via supply lines that come from supply reservoirs. Desired volumes of corresponding ingredients may then be suitably dispensed through outlet nozzles associated with pump regions. Alternatively, in another embodiment, tips suitable for storing desired amounts of volume are attached to outlets of pump regions and ingredients may be aspirated into tips from appropriate supply sources. Once a suitable volume of ingredient from corresponding supply sources is stored within corresponding tips that contain the ingredient, corresponding ingredients may be dispensed from the tips attached to the microfluidic chip. An example of suitable supply sources includes wells within a supply plate. As a result, instead of ingredients being supplied to diaphragm pumps within pump regions via supply lines, ingredients are supplied directly to tips attached to the microfluidic chip and subsequently dispensed into any appropriate region for receiving the ingredient, e.g., a well within a receiving plate.

Figure 13:
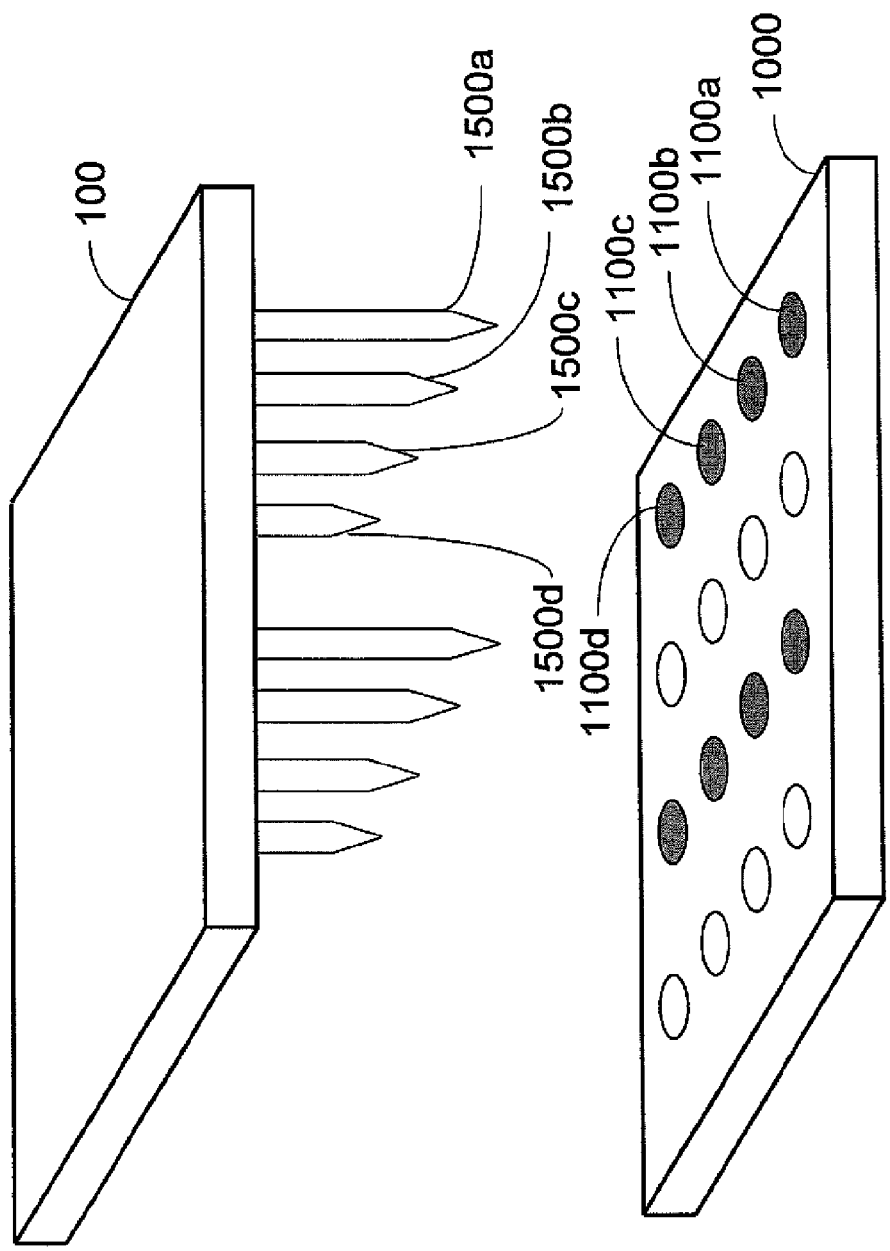
FIG. 13 is a schematic representation of a microfluidic dispensing system having removable dispensing tips according to one embodiment.

FIG. 13 shows an illustrative embodiment of microfluidic chip 100 incorporating tips 1500a, 1500b, 1500c, and 1500d, each of the tips corresponding to outlets of pump regions. Each of tips 1500a, 1500b, 1500c, and 1500d include a nozzle for fluid to flow past, entering or exiting the tip. In addition, supply plate 1000 is provided below microfluidic chip 100, the supply plate having a number of wells, including supply wells 1100a, 1100b, 1100c, and 1100d. Just as microfluidic chip 100 may incorporate any suitable number of pump regions, outlets, and associated tips, supply plate 1000 may incorporate any suitable number of supply wells.

It should be appreciated that any suitable tip may be used in aspirating ingredients from a supply source into the tip and subsequently dispensing those ingredients from the tip into a receiving region. In some embodiments, a microfluidic chip may be manufactured with tips that are permanently attached to outlets corresponding to pump regions disposed on the microfluidic chip. In some embodiments, tips may be temporarily or removeably attached to the microfluidic chip at outlets corresponding to appropriate pump regions. In this case, tips may be suitably connected to pump regions on the microfluidic chip and removed, as desired. In some embodiments, tips that may be removeably attached to the microfluidic chip may be disposable. Disposable tips that may be removeably attached may be advantageous in allowing for aspiration and dispense of ingredients without fear of contamination between different aspiration and dispense cycles.

Aspiration of ingredients into tips and dispense of ingredients from tips may occur through appropriate actuation of diaphragm pumps within pump regions of a microfluidic chip. For aspiration of ingredients, when the tip is placed in suitable contact with a supply ingredient, actuation of a diaphragm pump corresponding to that tip may provide a negative pressure gradient to be created within the tip so as to aspirate ingredient from a supply source into the tip. For dispense of ingredients, when the tip is appropriately positioned over a region for receiving the ingredient, actuation of a diaphragm pump corresponding to that tip may provide a positive pressure gradient to be created within the tip so as to dispense ingredient from the tip to the receiving region.

It should be appreciated that it is not necessary for the diaphragm pump corresponding to the ingredient to be aspirated and dispensed to come into contact with the corresponding ingredient. In some embodiments, a system fluid is provided in the pump region, the system fluid moving back and forth upon actuation of the appropriate diaphragm pump upon aspiration and dispensing. In this regard, upon aspiration, a system fluid is drawn into the diaphragm pump and a corresponding ingredient is drawn into the tip. Upon dispense, the system fluid is pushed out of the diaphragm pump and the corresponding ingredient is dispensed from the tip.

So that minimal contamination may occur, it may also be advantageous to aspirate in an air plug prior to aspiration of the supply ingredient. In this regard, a system fluid that may be present within the tip may be buffered from contact with the corresponding ingredient by the air plug. An air plug may be appropriately aspirated into the tip and an ingredient subsequently aspired into the tip. The air plug can thus act as a buffer between the system fluid and the ingredient.

It should also be appreciated that valves that provide for controlled fluid communication between diaphragm pumps and tips may also be appropriately utilized. In some embodiments, a valve is positioned between a tip and a corresponding diaphragm pump for suitable transfer of fluid between the tip and the corresponding diaphragm pump due to positive or negative pressure gradients created by the diaphragm pump. Fluid transferred between the tip and the corresponding diaphragm pump may be system fluid and/or ingredient. In some embodiments, a valve is positioned adjacent to the corresponding diaphragm pump providing access to a fluid reservoir where excess fluid, for example system fluid, may be displaced.

In some embodiments, a diaphragm pump may be surrounded by two valves, and upon use of the system to aspirate and dispense, both an air plug and an ingredient may be aspirated into a tip before subsequent dispensing of the ingredient. In addition, for some embodiments, corresponding pressure control pump signals are used for actuation of diaphragm pumps to fill and/or dispense. For some embodiments, corresponding pressure control valve signals are used for actuation of valves to provide fluid channels for fluid to flow between elements of a microfluidic chip.

More specifically, an embodiment will now be described where a diaphragm pump is surrounded by two valves and both an air plug and an ingredient are aspirated into a tip before subsequent dispensing of the ingredient. In this embodiment, an appropriate system fluid is provided throughout the fluid channels of the pump region and the tip. In addition, for this embodiment, the first valve is located between the tip and diaphragm pump and the second valve is located adjacent to the diaphragm pump to provide a fluid channel for excess fluid to flow. Much of the mechanics in actuation of the diaphragm pump and surrounding valves is captured in the description of FIGS. 12A-12F where fluid flows through fluid channels provided between valves and the diaphragm pump.

Prior to aspiration of an air plug or an ingredient, pressure control pump signals and pressure control valve signals are provided so as to close the first valve, the second valve, and the diaphragm pump. For aspiration of an air plug into the tip, a first opening pressure control valve signal for the air plug may be applied to the first valve in order to provide a fluid channel between the tip and the diaphragm pump. So that a negative pressure gradient may be created in the tip for aspirating an air plug into the tip, an opening pressure control pump signal for the air plug may be applied to the diaphragm pump for actuating the diaphragm pump and creating the negative pressure gradient in the tip for the air plug. While the air plug is aspirated in, the second valve that provides a channel for excess fluid flow remains closed.

In order to prepare the system for aspirating a subsequent ingredient behind the air plug, diaphragm pump should be closed without dispensing out the air plug. As such, a first closing pressure control valve signal may be applied to the first valve, actuating the first valve to close the fluid channel between the diaphragm pump and the tip. Next, a second opening pressure control valve signal may be applied to the second valve, actuating the valve and providing a fluid channel from the diaphragm pump to a fluid reservoir, such as for example, a corresponding supply line, for excess system fluid to flow. A closing pressure control pump signal may then be applied, displacing system fluid out of the pump space and through the fluid channel provided by the second valve. Once the diaphragm pump is emptied, then a second closing pressure control valve signal may be applied to the second valve for closing the fluid channel between the diaphragm pump and the fluid reservoir for drawing excess fluid.

Now, with the system fluid appropriately displaced, an ingredient may be aspirated into the tip. Similarly as for aspiration of the air plug, a first opening pressure control valve signal for the ingredient may be applied to the first valve in order to provide a fluid channel between the tip and the diaphragm pump. So that a negative pressure gradient may be created in the tip for aspirating the ingredient into the tip, an opening pressure control pump signal for the ingredient may be applied to the diaphragm pump for actuating the diaphragm pump and creating the negative pressure gradient in the tip for the ingredient. While the ingredient is aspirated in behind the air plug, the second valve that provides a channel for excess fluid flow remains closed.

It should be appreciated that pressure control pump signals and pressure control valve signals for aspirating or dispensing different ingredients and/or air plugs may be different. In some embodiments, for example, because some ingredients may be more viscous than air and, hence, may require more force to aspirate, an opening pressure control pump signal for an air plug may be less than an opening pressure control pump signal for an ingredient. Also, in some embodiments, an opening pressure control pump signal for one ingredient may be more or less than an opening pressure control pump signal for a different ingredient. Similarly, closing pressure control pump signals may vary accordingly depending on the ingredient(s) in comparison to one another and air plugs. In some embodiments, pressure control pump signals and/or pressure control valve signals may be pneumatic in nature. In some embodiments, pressure control pump signals and/or pressure control valve signals may be hydraulic in nature.

So that a greater volume of ingredient than is provided for by the pump space is aspirated into the tip, another volume of ingredient equivalent to the pump space of the diaphragm pump may be subsequently aspirated behind the first volume of ingredient. Similar to that described above, a first closing pressure control valve signal may be applied to the first valve, actuating the first valve to close the fluid channel between the diaphragm pump and the tip. Next, a second opening pressure control valve signal may be applied to the second valve, actuating the valve and providing a fluid channel from the diaphragm pump to a fluid reservoir, such as for example, a corresponding supply line, for excess system fluid to flow. A closing pressure control pump signal may then be applied, displacing system fluid out of the pump space and through the fluid channel provided by the second valve. Once the diaphragm pump is emptied, then a second closing pressure control valve signal may be applied to the second valve for closing the fluid channel between the diaphragm pump and the fluid reservoir for drawing excess fluid.

Again, when system fluid is appropriately displaced, a subsequent volume of ingredient may be aspirated into the tip. Similarly as for aspiration of the previous volume of ingredient, a first opening pressure control valve signal for the ingredient may be applied to the first valve in order to provide a fluid channel between the tip and the diaphragm pump. So that a negative pressure gradient may be created in the tip for aspirating the ingredient into the tip, an opening pressure control pump signal for the ingredient may be applied to the diaphragm pump for actuating the diaphragm pump and creating the negative pressure gradient in the tip for the ingredient. While the next volume of ingredient is aspirated in behind the previous volume of ingredient, the second valve that provides a channel for excess fluid flow remains closed.

It can be appreciated that any number of subsequent volumes of ingredient may be aspirated by appropriately repeating the above steps until a desired final volume of ingredient is aspirated into the tip.

Once the desired final volume of ingredient is disposed in the tip, the ingredient may then be dispensed. Similarly to the way the ingredient is aspirated into the tip pump volume by pump volume, the ingredient may be dispensed from the tip pump volume by pump volume. Again, actuation of the diaphragm pump and associated valves leading to appropriate displacement of system fluid allow for the ingredient to be suitably dispensed.

Prior to dispense of the ingredient from the tip, pressure control pump signals and pressure control valve signals are provided so as to close the first valve, the second valve, and the diaphragm pump. For dispense of a portion of the ingredient from the tip, a second opening pressure control valve signal may be applied to the second valve in order to provide a fluid channel between the fluid reservoir having excess system fluid and the diaphragm pump. An opening pressure control pump signal may be applied to the diaphragm pump for actuating the diaphragm pump, filling the pump space of the diaphragm pump with system fluid, and preparing the diaphragm pump for eventually creating a positive pressure gradient in the tip. A second closing pressure control valve signal may then be applied to the second valve in closing the fluid channel off between the diaphragm pump and the fluid reservoir for excess system fluid.

Now that the diaphragm pump is filled and primed for exerting pressure for dispensing ingredient out of the tip, a first opening pressure control valve signal may be applied to the first valve in order to provide a fluid channel between the tip and the diaphragm pump. So that a positive pressure gradient may be created in the tip for dispensing a portion of the ingredient from the tip, a closing pressure control pump signal for the ingredient may be applied to the diaphragm pump for actuating the diaphragm pump and creating the positive pressure gradient in the tip for the ingredient. While that portion of the ingredient is dispensed from the tip, the second valve that provides a channel for excess fluid flow remains closed so that no back flow of system fluid occurs. A first closing pressure control valve signal is then applied to the first valve for closing the fluid channel between the tip and the diaphragm pump.

It can be appreciated that any number of subsequent volumes of ingredient may be dispensed from the tip by appropriately repeating the above steps of displacing system fluid and dispensing ingredient from the tip until the desired amount of ingredient is dispensed from the tip.

It can also be appreciated that any suitable configuration of valves around one or more diaphragm pumps may be utilized for aspiration of an ingredient into a tip and subsequent dispense from the tip. Indeed, it is not a necessary aspect of that presented herein to have valves for aspiration of an ingredient into a tip and subsequent dispense from the tip.

FIGS. 14A-14G show an illustrative embodiment of a number of tips attached to a microfluidic chip, aspirating ingredients into corresponding tips and dispensing of corresponding ingredients out of the tips. In some embodiments, aspiration of air plugs into a number of tips may occur simultaneously. In some embodiments, aspiration of various ingredients into a number of corresponding tips may occur simultaneously. In some embodiments, dispensing of ingredients from a number of corresponding tips may occur simultaneously.

Figure 14A:
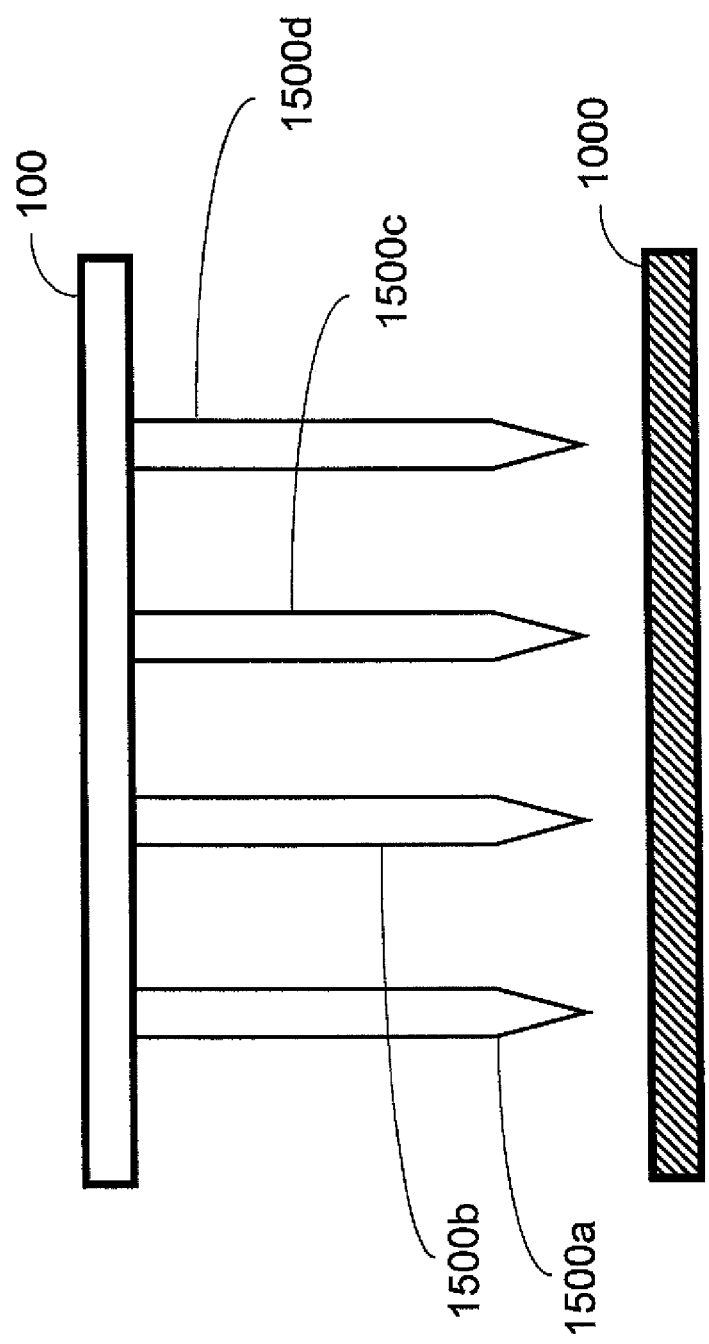
FIG. 14A is a schematic side view representation of a microfluidic dispensing system having removable dispensing tips according to one embodiment.

In the embodiment shown in FIG. 14A, tips 1500a, 1500b, 1500c, and 1500d are attached to microfluidic chip 100 and are disposed above supply wells (not shown) on supply plate 1000. Tips 1500a, 1500b, 1500c, and 1500d are in fluid communication with outlets of pump regions in microfluidic chip 100 where diaphragm pumps are used for providing aspirating and dispensing pressure to the tips.

Figure 14B:
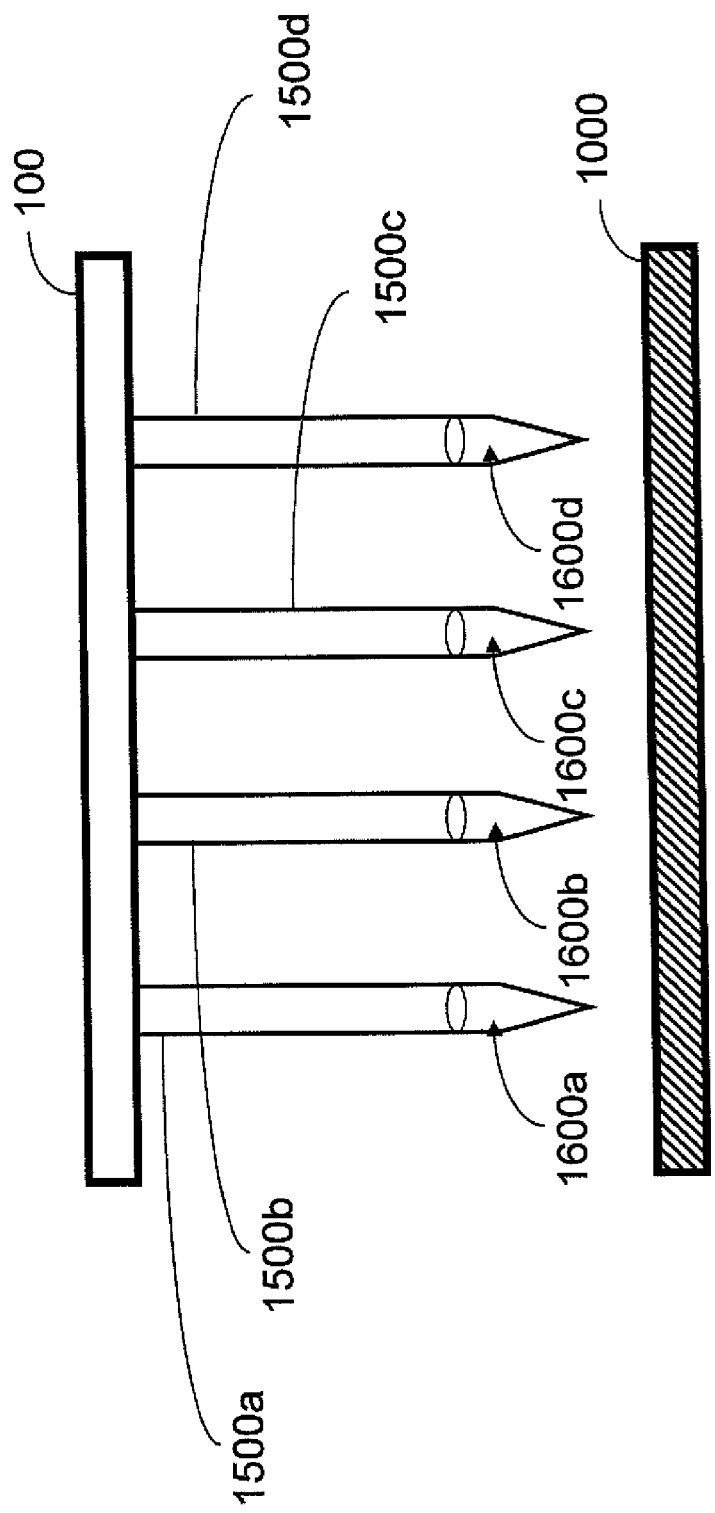
FIG. 14B is a schematic side view representation of a microfluidic dispensing system showing the tips aspirating air plugs according to one embodiment.

Shown in FIG. 14B, diaphragm pumps within pump regions on microfluidic chip 100 are actuated to create a negative pressure gradient in corresponding tips 1500a, 1500b, 1500c, and 1500d. As a result, air plugs 1600a, 1600b, 1600c, and 1600d are aspirated into corresponding tips 1500a, 1500b, 1500c, and 1500d.

Figure 14C:
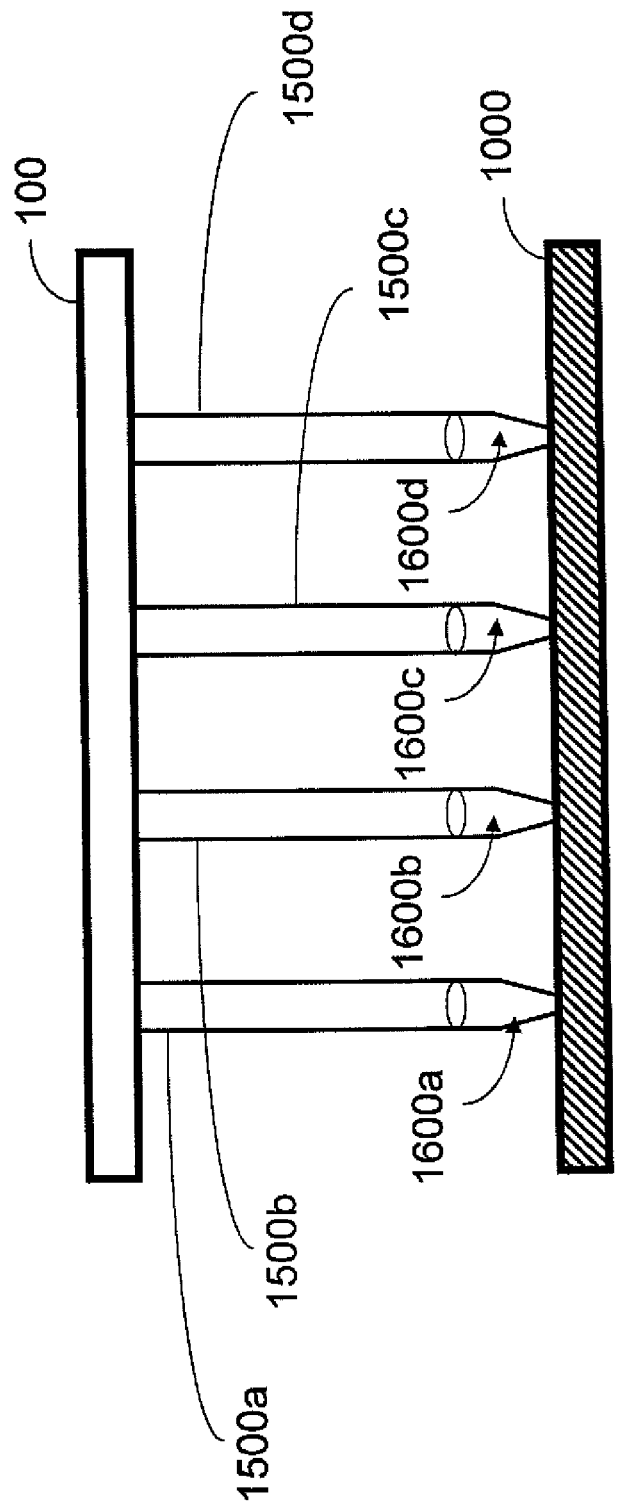
FIG. 14C is a schematic side view representation of a microfluidic dispensing system showing the tips contacting corresponding ingredients according to one embodiment.

Microfluidic chip 100 is then lowered toward supply plate 1000, as depicted in FIG. 14C, so that tips 1500a, 1500b, 1500c, and 1500d descend into supply wells of supply plate 1000. As a result, tips 1500a, 500b, 1500c, and 1500d are placed in contact with ingredients stored in the corresponding supply wells (not shown).

Figure 14D:
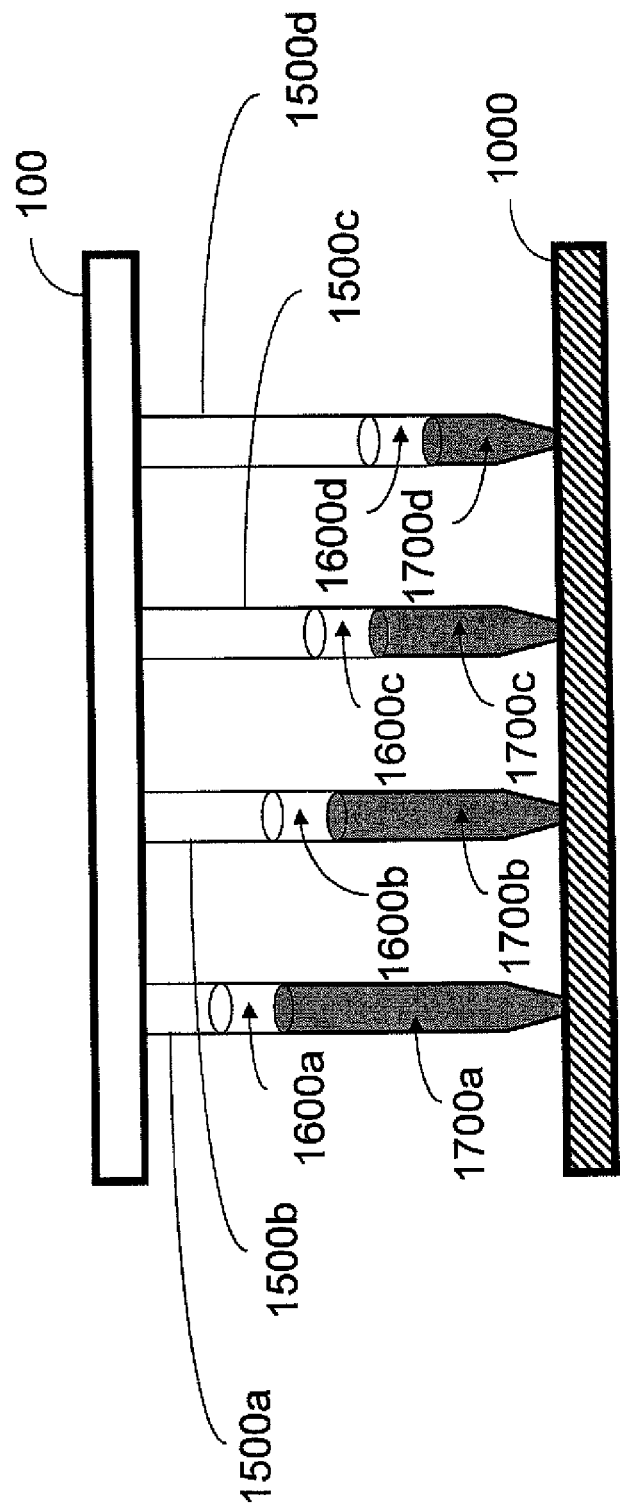
FIG. 14D is a schematic side view representation of a microfluidic dispensing system with the tips aspirating corresponding ingredients according to one embodiment.

As depicted in FIG. 14D, diaphragm pumps within pump regions on microfluidic chip 100 are actuated to create a negative pressure gradient in corresponding tips 1500a, 1500b, 1500c, and 1500d. As a result, corresponding ingredients 1700a, 1700b, 1700c, and 1700d are aspirated into corresponding tips 1500a, 1500b, 1500c, and 1500d. Ingredients 1700a, 1700b, 1700c, and 1700d that are aspirated into corresponding tips 1500a, 1500b, 1500c, and 1500d may be of varying volumes, depending on the desired amount of ingredient to be stored in tips 1500a, 1500b, 1500c, and 1500d to be eventually dispensed. As described above, in some embodiments, diaphragm pumps may be actuated multiple times in order to aspirate in the desired volume of ingredient into corresponding tips. However, in some embodiments, diaphragm pumps for corresponding tips 1500a, 1500b, 1500c, and 1500d may be of appropriately different sizes. Due to variation in pump space of corresponding diaphragm pumps, the number of repeated aspiration steps may vary accordingly to the desired amount of ingredient to be stored in corresponding tips 1500a, 1500b, 1500c, and 1500d.

Figure 14E:
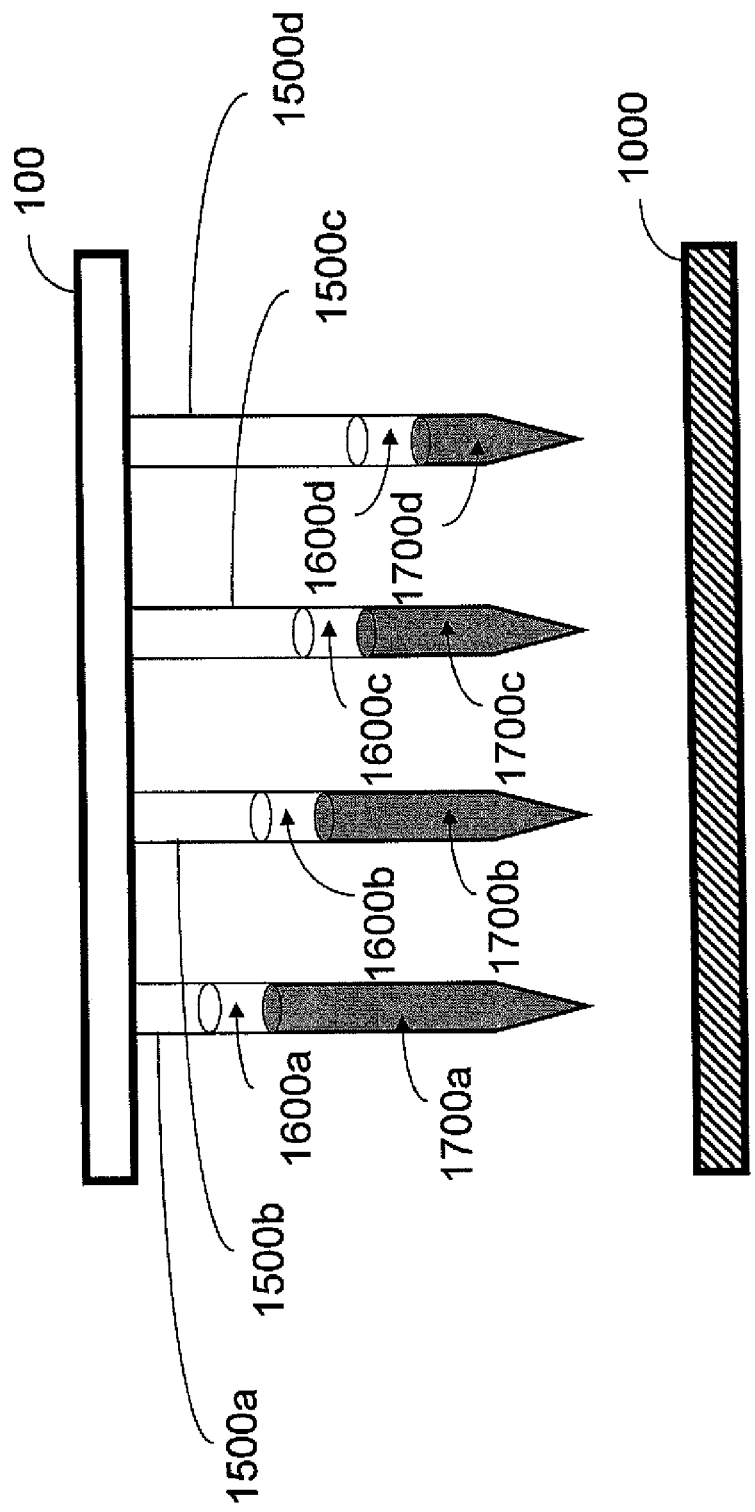
FIG. 14E is a schematic side view representation of a microfluidic dispensing system with the tips containing the corresponding ingredients and air plugs according to one embodiment.
Figure 14F:
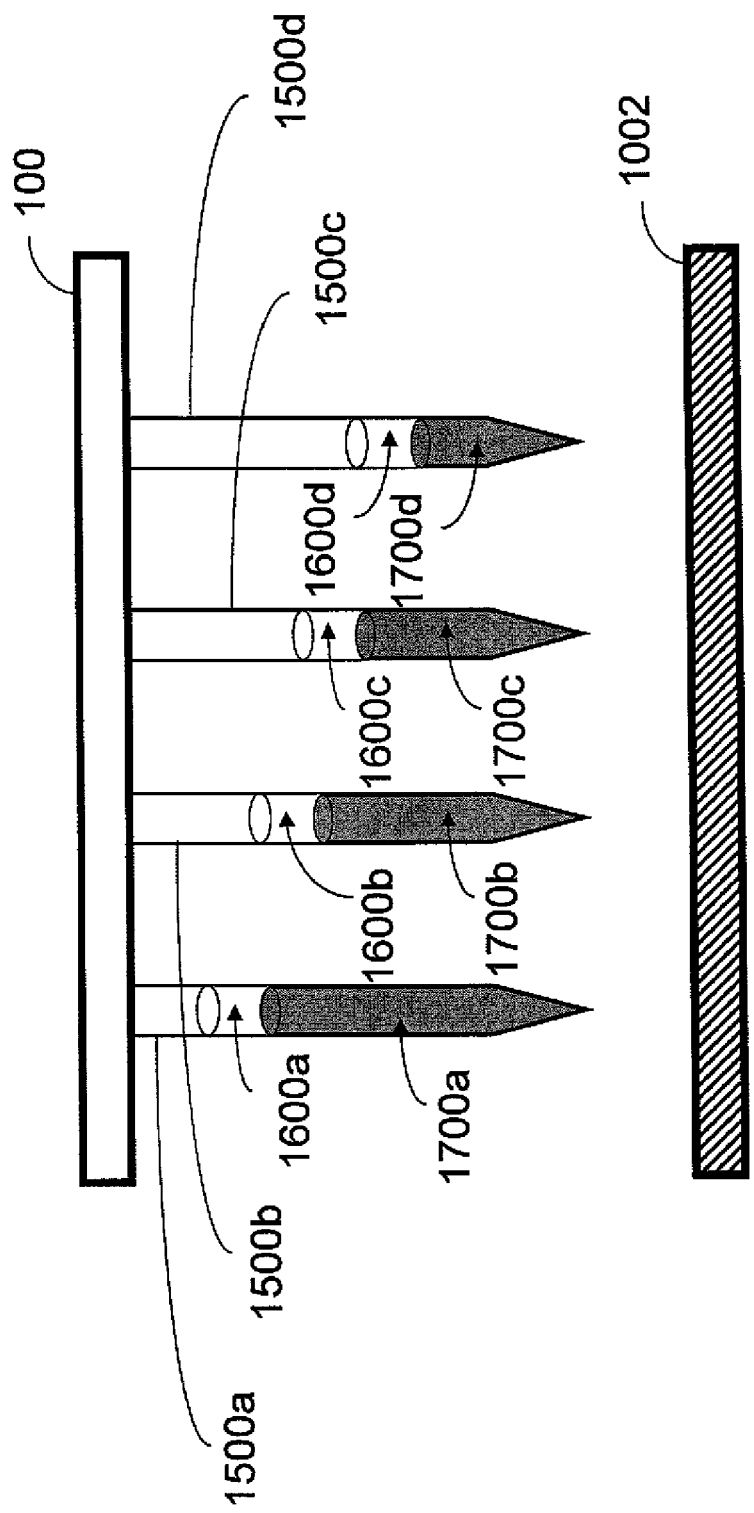
FIG. 14F is a schematic side view representation of a microfluidic dispensing system showing the tips above a multiwell plate.

FIG. 14E shows microfluidic chip 100 being raised from supply plate 1000 so that tips 1500a, 1500b, 1500c, and 1500d are no longer in contact with ingredients stored in corresponding supply wells. However, air plugs and ingredients stored in corresponding tips 1500a, 1500b, 1500c, and 1500d remain. Microfluidic chip 100 is then appropriately maneuvered such that it is no longer disposed above supply plate 1000, but instead, is disposed above receiving plate 1002, as depicted in FIG. 14F.

Figure 14G:
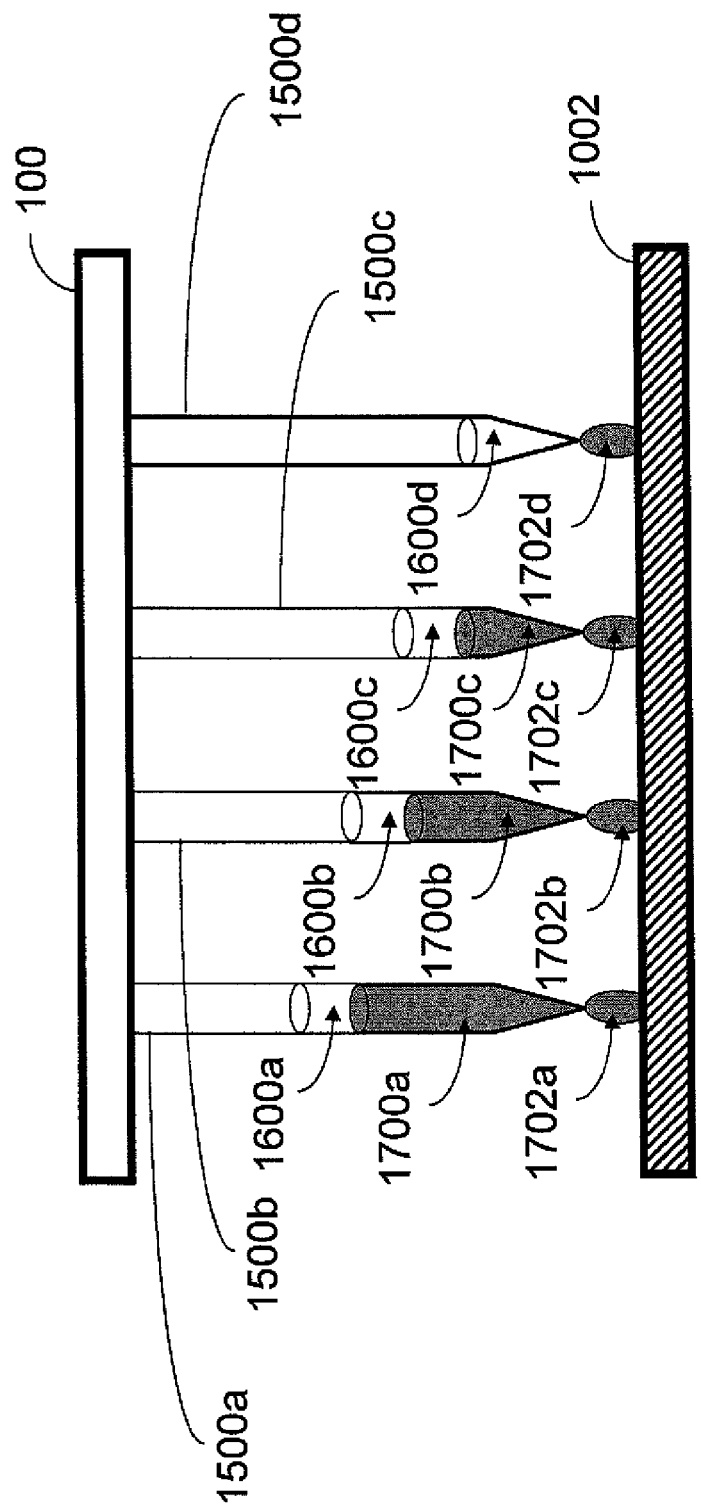
FIG. 14G is a schematic side view representation of a microfluidic dispensing system showing dispensing the corresponding ingredients into the multiwell plate.

As next shown in FIG. 14G, microfluidic chip 100 is appropriately maneuvered so that ingredients 1700a, 1700b, 1700c, and 1700d disposed in corresponding tip 1500a, 1500b, 1500c, and 1500d are suitably positioned above a dispense plate 1002. Corresponding diaphragm pumps within pump regions of microfluidic chip 100 are actuated to dispense ingredients 1700a, 1700b, 1700c, and 1700d from corresponding tips 1500a, 1500b, 1500c, and 1500d. Dispensed ingredients 1702a, 1702b, 1702c, and 1702d are then received by corresponding wells (not shown) of a receiving plate 1002.

It can be appreciated that a supply plate 1000 may be the same multiwell plate as a receiving plate 1002. Tips from microfluidic chip 100 may aspirate ingredients from supply wells at one region of the multiwell plate and dispense those ingredients into receiving wells at another region of the multiwell plate.

The foregoing written specification is to be considered to be sufficient to enable one skilled in the art to practice the invention. While the best mode for carrying out the invention has been described in detail, those skilled in the art to which this invention relates will recognize various alternative embodiments including those mentioned above as defined by the following claims. The examples disclosed herein are not to be construed as limiting of the invention as they are intended merely as illustrative of particular embodiments of the invention as enabled herein. Therefore, systems and methods that are functionally equivalent to those described herein are within the spirit and scope of the claims appended hereto. Indeed, various modifications of the invention in addition to those shown and described herein will become apparent to those skilled in the art from the foregoing description and fall within the scope of the appended claims.

What is claimed is:

1. A microfluidic dispensing system, the system comprising:
   a plurality of diaphragm pumps, each of the plurality of diaphragm pumps configured to be actuated upon application of a corresponding pressure control pump signal, and each of the plurality of diaphragm pumps constructed and arranged to pump a fixed volume of fluid;
   a plurality of supply lines, each of the supply lines being in fluid communication with at least one of the diaphragm pumps and configured to simultaneously supply a corresponding ingredient to the at least one of the diaphragm pumps, wherein each of the corresponding ingredients comes from a different supply reservoir corresponding to each of the supply lines and wherein each of the supply lines forms a fluid channel between the supply reservoir and the at least one of the diaphragm pumps; and
   an array of nozzles separate from the plurality of supply lines and in fluid communication with the at least one of the diaphragm pumps and configured to simultaneously dispense the corresponding ingredient in each of the at least one of the diaphragm pumps upon application of the corresponding pressure control pump signal.

2. The microfluidic dispensing system of claim 1, wherein each of the plurality of diaphragm pumps is elastomeric.

3. The microfluidic dispensing system of claim 1, wherein the corresponding pressure control pump signal comprises a vacuum.

4. The microfluidic dispensing system of claim 1, further comprising a fluid access port adjacent to each of the plurality of diaphragm pumps, wherein upon application of the corresponding pressure control pump signal, the corresponding ingredient flows through the fluid access port.

5. The microfluidic dispensing system of claim 1, further comprising:
   at least one first valve corresponding to each of the plurality of diaphragm pumps and being actuated upon application of a corresponding first pressure control valve signal, the at least one first valve providing a first fluid channel to and from the corresponding diaphragm pump; and
   a plurality of fluid access ports adjacent to the at least one first valve.

6. The microfluidic dispensing system of claim 5, wherein the at least one first valve is elastomeric.

7. The microfluidic dispensing system of claim 5, wherein the corresponding first pressure control valve signal comprises a vacuum.

8. The microfluidic dispensing system of claim 5, further comprising:
   at least one second valve being actuated upon application of a corresponding second pressure control valve signal, the at least one second valve providing a second fluid channel to and from the corresponding diaphragm pump; and
   a plurality of fluid access ports adjacent to the at least one second valve.

9. The microfluidic dispensing system of claim 8, wherein the at least one second valve is elastomeric.

10. The microfluidic dispensing system of claim 8, wherein the corresponding second pressure control valve signal comprises a vacuum.

11. The microfluidic dispensing system of claim 1, wherein each of the plurality of supply lines comprises an inlet adapted to couple the supply line with at least one supply reservoir to establish fluid communication therebetween.

12. The micro fluidic dispensing system of claim 11, wherein the at least one supply reservoir comprises a supply bottle.

13. The microfluidic dispensing system of claim 11, wherein each inlet of each of the plurality of supply lines comprises a magnetic portion adapted magnetically couple the supply line with the at least one supply reservoir to establish fluid communication therebetween.

14. The microfluidic dispensing system of claim 1, wherein each of the plurality of diaphragm pumps is configured to draw the corresponding ingredient from the supply reservoir.

* * * * *